United States Patent
Mallampalli et al.

(10) Patent No.: US 11,242,339 B2
(45) Date of Patent: Feb. 8, 2022

(54) CHEMICAL INHIBITION OF THE E3 LIGASE SUBUNIT FBXO7 CONFERS NEUROPROTECTION AND ANTI-INFLAMMATORY ACTIVITY BY STABILIZING MITOCHONDRIA

(71) Applicants: University of Pittsburgh—Of the Commonwealth System of Higher Education, Pittsburgh, PA (US); The United States Government as represented by the Department of Veterans Affairs, Washington, DC (US)

(72) Inventors: Rama K. Mallampalli, Sewickley, PA (US); Beibei Chen, Sewickley, PA (US); Charleen T. Chu, Wexford, PA (US); Yuan Liu, Sewickley, PA (US)

(73) Assignees: University of Pittsburgh—Of the Commonwealth System of Higher Education, Pittsburgh, PA (US); The United States Government as represented by the Department of Veterans Affairs, Washington, DC (US)

( * ) Notice: Subject to any disclaimer, the term of this patent is extended or adjusted under 35 U.S.C. 154(b) by 38 days.

(21) Appl. No.: 16/624,843

(22) PCT Filed: Jun. 25, 2018

(86) PCT No.: PCT/US2018/039327
§ 371 (c)(1),
(2) Date: Dec. 19, 2019

(87) PCT Pub. No.: WO2019/005685
PCT Pub. Date: Jan. 3, 2019

(65) Prior Publication Data
US 2020/0216426 A1 Jul. 9, 2020

Related U.S. Application Data

(60) Provisional application No. 62/527,492, filed on Jun. 30, 2017.

(51) Int. Cl.
| | | |
|---|---|---|
| *C07D 405/12* | (2006.01) | |
| *A61P 25/28* | (2006.01) | |
| *A61P 25/16* | (2006.01) | |
| *A61K 31/517* | (2006.01) | |

(52) U.S. Cl.
CPC .......... *C07D 405/12* (2013.01); *A61K 31/517* (2013.01); *A61P 25/16* (2018.01); *A61P 25/28* (2018.01)

(58) Field of Classification Search
CPC ........ C07D 405/12; A61P 25/28; A61P 25/16; A61P 43/00; A61P 9/00; A61P 21/00; A61P 29/00; A61K 31/517
See application file for complete search history.

(56) References Cited

U.S. PATENT DOCUMENTS

| | | |
|---|---|---|
| 3,127,401 A | 3/1964 | Lawes et al. |
| 2009/0163545 A1 | 6/2009 | Goldfarb |

FOREIGN PATENT DOCUMENTS

| | | |
|---|---|---|
| WO | WO 2007/022946 | 3/2007 |
| WO | WO 2007/062817 | 6/2007 |

OTHER PUBLICATIONS

CAS Registry No. 422283-27-0 entered May 28, 2002.
PubChem CID 644437 created Jun. 4, 2005.
PubChem CID 2192714 created Jul. 15, 2005.
PubChem CID 2550870 created Jul. 16, 2005.
PubChem CID 2567018 created Jul. 16, 2005.
PubChem CID 2883205 created Jul. 29, 2005.

(Continued)

*Primary Examiner* — Robert H Havlin
(74) *Attorney, Agent, or Firm* — Klarquist Sparkman, LLP

(57) ABSTRACT

A method for treating a neurodegenerative disease or an inflammatory disorder in a subject, comprising administering to the subject in need thereof, a compound, or a pharmaceutically acceptable salt thereof, of formula II:

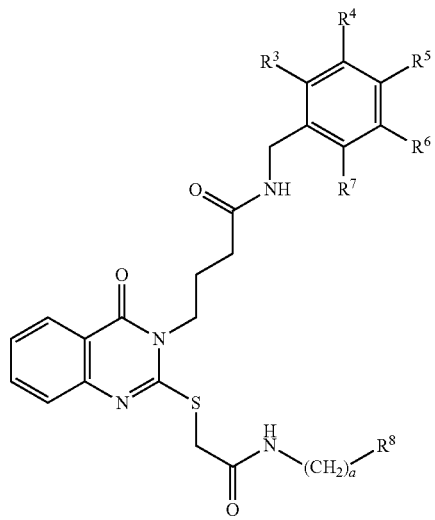

wherein each of $R^3$-$R^7$ is independently H, halogen, optionally-substituted alkyl, amino, alkoxy or hydroxy;
$R^8$ is an optionally-substituted heterocycloalkyl; and
a is 0 to 3.

21 Claims, 28 Drawing Sheets

(56) References Cited

OTHER PUBLICATIONS

PubChem CID 2998206 created Jul. 30, 2005.
PubChem CID 3237459 created Aug. 16, 2005.
PubChem CID 3244833 created Aug. 16, 2005.
PubChem CID 9551128 created Oct. 20, 2006.
International Search Report and Written Opinion issued for International Application No. PCT/US2018/039327 dated Oct. 4, 2018.
Landre et al., "Screening for E3-ubiquitin ligase inhibitors: challenges and opportunities," *Oncotarget*, 5(18): 7988-8013, Sep. 3, 2014.
PubChem AID: 624263, "A quantitative high throughput screen to identify chemical modulators of PINK1 expression," PubChem BioAssay Database, National Center for Biotechnology Information. Deposit Date: Jun. 5, 2012.
PubChem AID: 777, "CYP2C9 Assay," PubChem BioAssay Database, National Center for Biotechnology Information. Deposit Date: Jul. 13, 2007.
Yoshikawa et al., "Optimized method of G-protein-coupled receptor homology modeling: its application to the discovery of novel CXCR7 ligands," *J. Med. Chem.*, 56(11): 4236-4251, May 8, 2013.

FIG. 1D
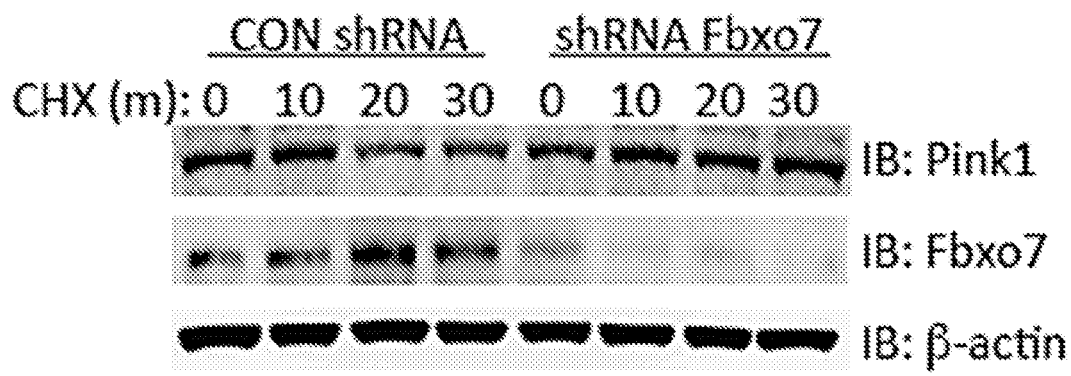
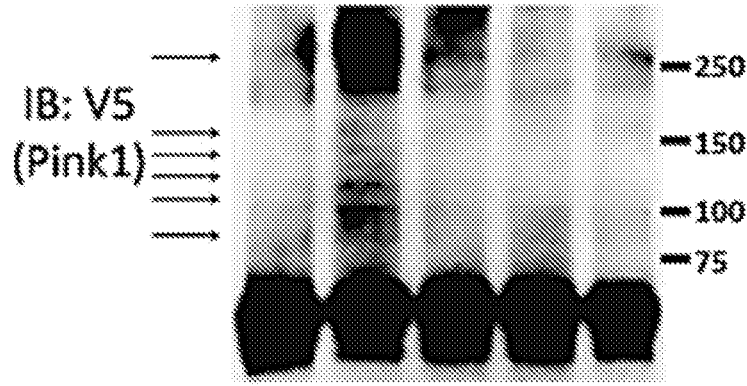
FIG. 1E

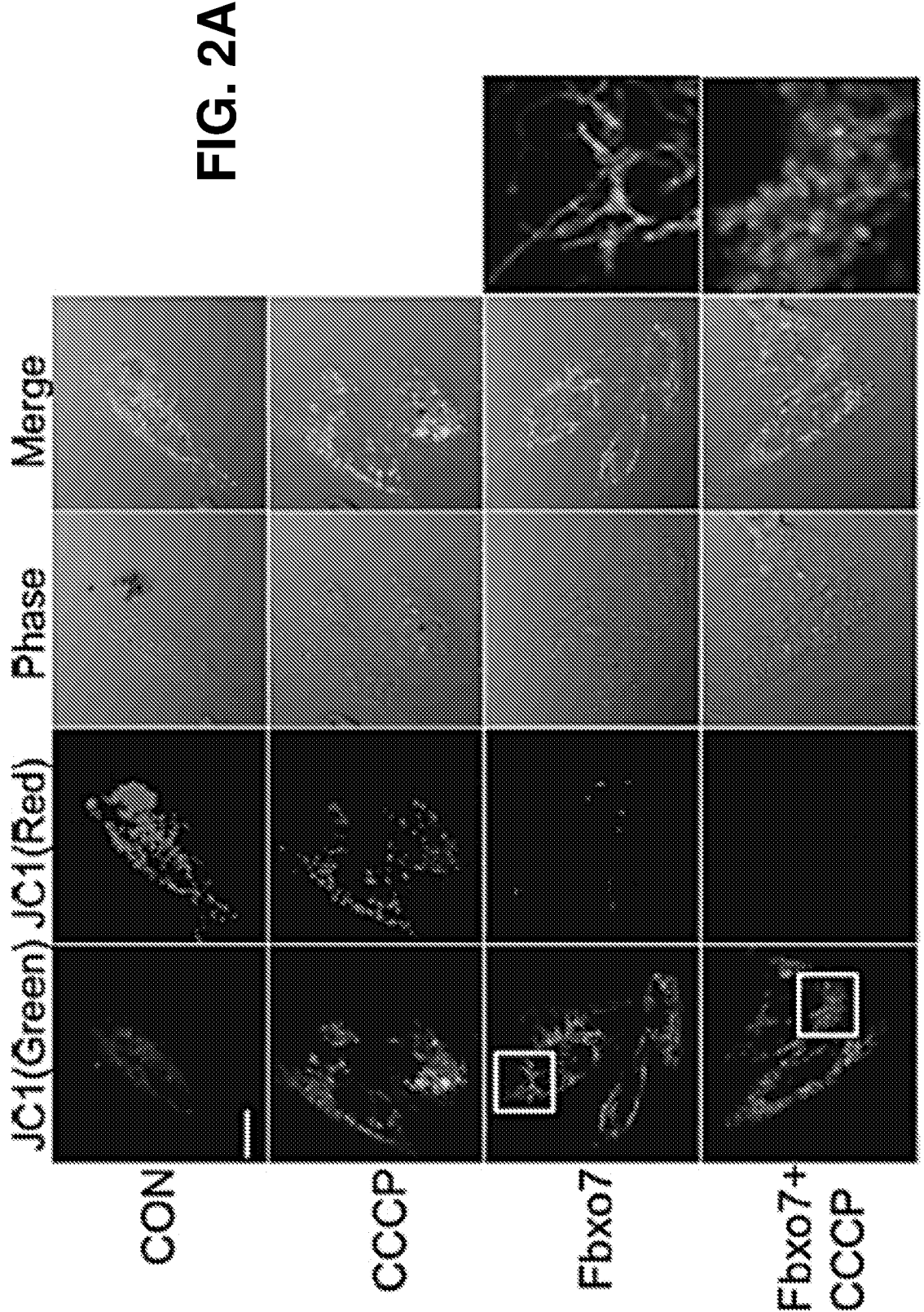

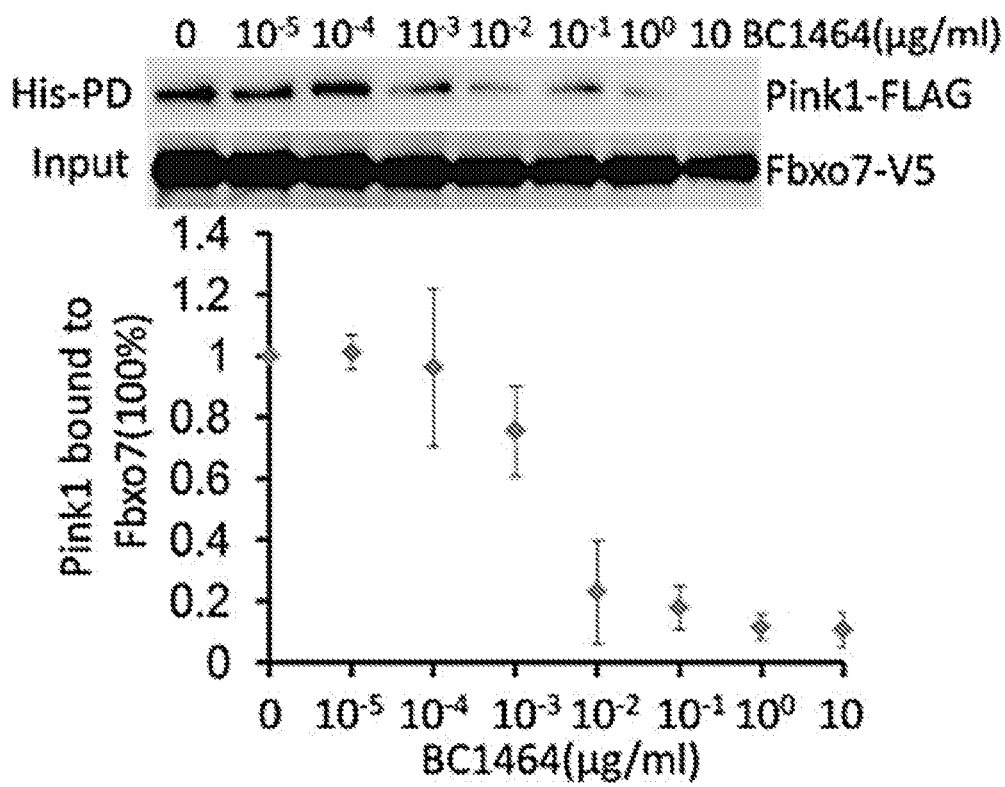
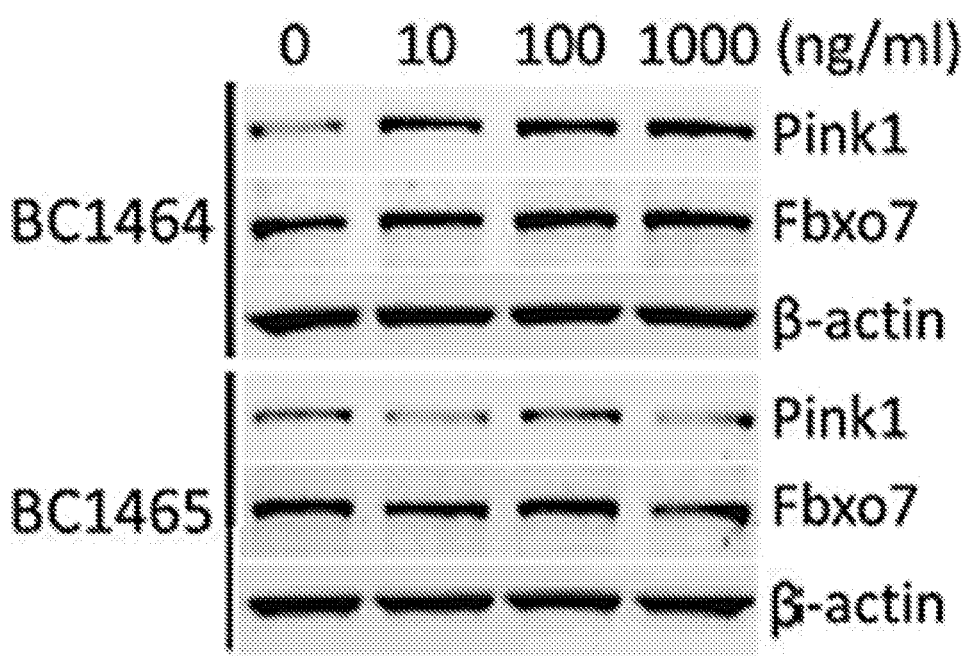

FIG. 7B
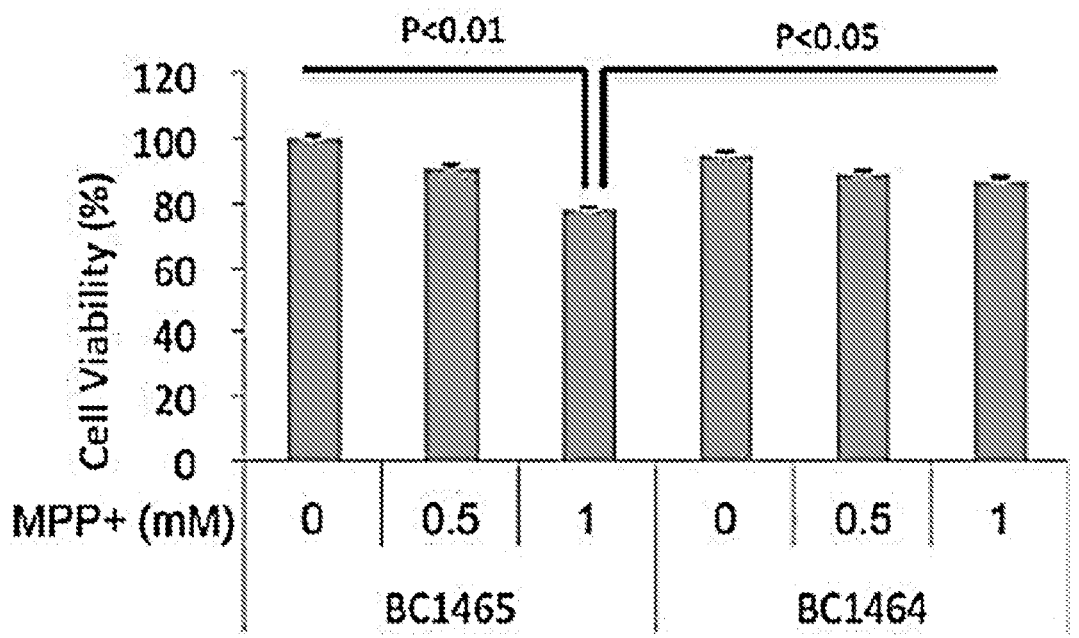
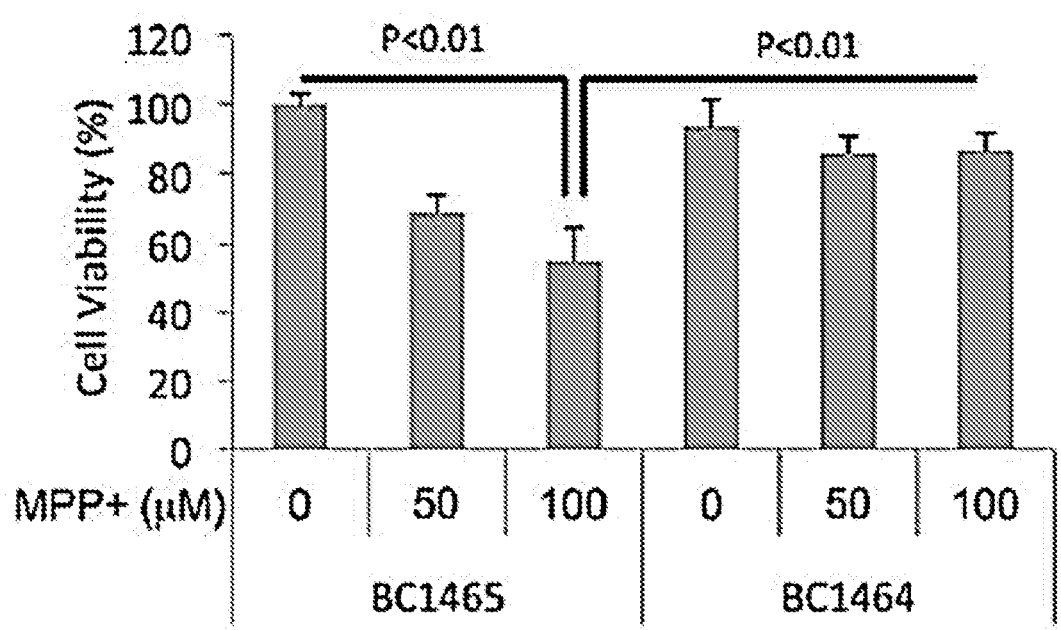
FIG. 7C

CHEMICAL INHIBITION OF THE E3 LIGASE SUBUNIT FBXO7 CONFERS NEUROPROTECTION AND ANTI-INFLAMMATORY ACTIVITY BY STABILIZING MITOCHONDRIA

CROSS REFERENCE TO RELATED APPLICATIONS

This is the U.S. National Stage of International Application No. PCT/US2018/039327, filed Jun. 25, 2018, which was published in English under PCT Article 21(2), which application in turn claims the benefit of U.S. Provisional Application No. 62/527,492, filed Jun. 30, 2017, which is herein incorporated by reference in its entirety.

ACKNOWLEDGMENT OF GOVERNMENT SUPPORT

This invention was made with government support under Grant Numbers HL116472, NS065789, AG026389, HL114453, HL081784, HL098174, HL097376, HL132862, HL096376 and $R^{01}$ NS101628 awarded by the National Institutes of Health. The government has certain rights in the invention.

This work was supported by the United States Department of Veterans Affairs, Veterans Health Administration, Office of Research and Development under a Merit Award from the Biomedical Laboratory Research and Development Program.

BACKGROUND

PTEN-induced putative kinase 1 (Pink1) is a serine/threonine protein kinase encoded by the Pink1 gene. Pink1 functions in a critical important role for the maintenance of high quality mitochondria, through its effects on dynamics, function and the selective degradation of damaged mitochondria through mitophagy. Loss of function mutations in the Pink1 gene cause mitochondrial dysfunction and an early onset familial form of Parkinson's disease. Pink1 deficiency models in *Drosophila* and zebrafish, and the in vitro knockdown of Pink1, result in significant mitochondrial dysfunction including reduction of electron transport chain (ETC) function, defective mitochondrial dynamics, increased oxidative stress, altered mitophagy, and cell death.

Pink1 deficiency has also been shown to enhance release of inflammatory cytokines (including TNF-α, IL-1β, and IL-6) after injury in the brain, by an NF-κB-dependent mechanism. These inflammatory responses are more severe in Pink1-deficient mice than in control littermates, as determined by elevated mRNA levels of the pro-inflammatory cytokines TNF-α and IL-6 and decreased anti-inflammatory cytokines such as IL-10. These observations suggest that approaches that maintain or increase Pink1 protein concentrations in cells might provide important opportunities to preserve chemical energy stores during stress, limiting neurodegeneration, cell death and inflammation. Yet to date there are no chemical entities that increase Pink1 levels in cells.

Cellular protein abundance is highly regulated by the ubiquitin proteasome system that eliminates proteins by selective degradation. Ubiquitin conjugation to a target protein is orchestrated by an enzymatic cascade involving an E1 ubiquitin activating enzyme, an E2 ubiquitin conjugating enzyme, and an E3 ubiquitin ligase, generating an isopeptide bond between the C-terminus of ubiquitin and the substrate's ε-amino lysine. Of more than 1,000 E3 ligases, the Skp-Cullin1-F-box (SCF) type E3 ligase plays diverse roles in cancer, cell cycle progression, gene expression, and inflammation. The SCF complex contains a catalytic core consisting of Skp1, Cullin1, and Rbx1, and an adaptor receptor subunit F-box protein, which recruits substrates to the E3 catalytic core. F-box proteins are categorized into three families based on their substrate-binding motif. The L family F-box protein is characteristic of a leucine-rich repeat (LRR) motif; the W family contains a WD repeat motif; and the O family contains a variety of unknown motifs. Through these substrate binding motifs, the F-box protein recognizes and recruits substrates in a highly selective manner in response to specific stimuli in different tissues. However, only a few F box proteins are well characterized with regard to both their molecular behavior and impact in human biology. Interestingly, one F-box protein, Fbxo7, partakes in mitophagy in response to mitochondrial damage by interacting with Pink1. Further, mutations in the gene encoding Fbxo7 have been identified in families with Parkinson's disease similar to that caused by mutations in Pink1. In one study, Fbxo7 binds and targets neurotrophin receptor-interacting MAGE (NRAGE) to mediate its polyubiquitylation in cells thereby activating NF-κB activity in cells, underscoring a potential role for the F box protein in disease pathogenesis. Mice defective in Fbxo7 expression also exhibit hematological abnormalities. Taken together, the data suggest that the biological role of Fbxo7 is not well characterized and the functional consequences for Fbxo7 interaction with Pink1 requires further study.

SUMMARY

Disclosed herein are compounds, or pharmaceutically acceptable salts thereof, of formula I:

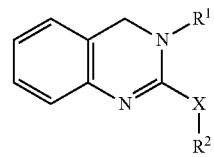

wherein $R^1$ and $R^2$ are each independently optionally-substituted alkyl, optionally-substituted aryl, amino, optionally-substituted heterocyclic, acyl, aminocarbonyl, carbonylamino, or substituted thiol; and X is S or CH$_2$; provided that the compound is not

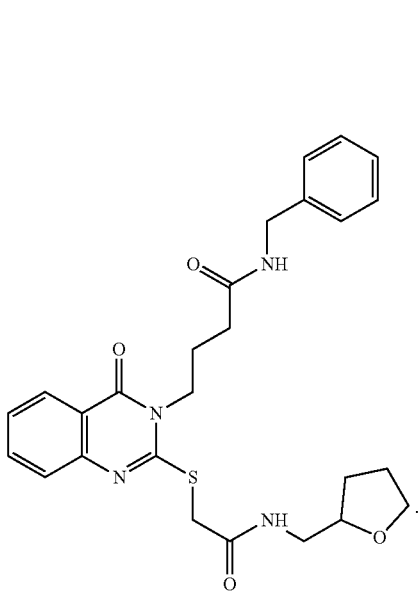

Also disclosed herein are compounds, or pharmaceutically acceptable salts thereof, of formula II:

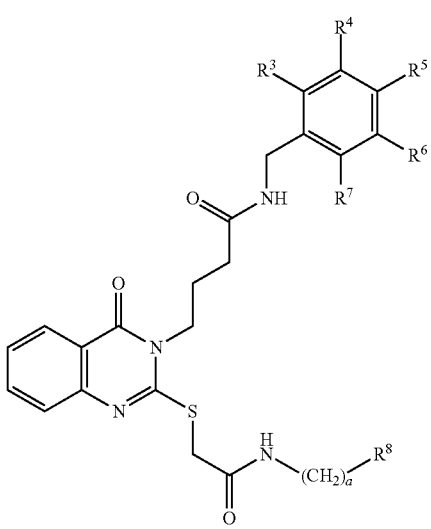

wherein each of R$^3$-R$^7$ is independently H, halogen, optionally-substituted alkyl, amino, alkoxy or hydroxy;

R$^8$ is an optionally-substituted heterocycloalkyl; and a is 0 to 3; provided that the compound is not

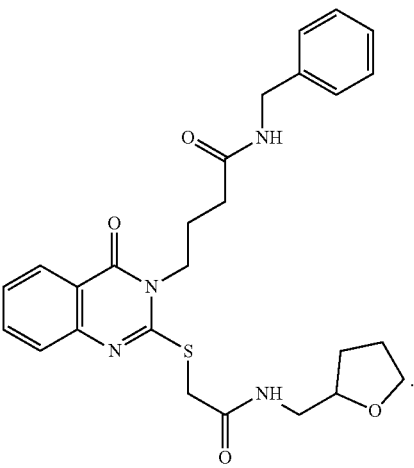 [SMILES: O=C(CCCn1c(SCC(=O)NCC2CCCO2)nc2ccccc2c1=O)NCc1ccccc1]

Also disclosed herein is a method for treating a neurodegenerative disease or an inflammatory disorder in a subject, comprising administering to the subject in need thereof, a compound, or a pharmaceutically acceptable salt thereof, of formula I:

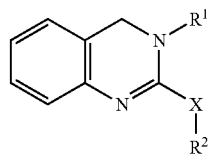

wherein R$^1$ and R$^2$ are each independently optionally-substituted alkyl, optionally-substituted aryl, amino, optionally-substituted heterocyclic, acyl, aminocarbonyl, carbonylamino, or substituted thiol; and X is S or CH$_2$.

Further disclosed herein is a method for treating a neurodegenerative disease or an inflammatory disorder in a subject, comprising administering to the subject in need thereof, a compound, or a pharmaceutically acceptable salt thereof, of formula II:

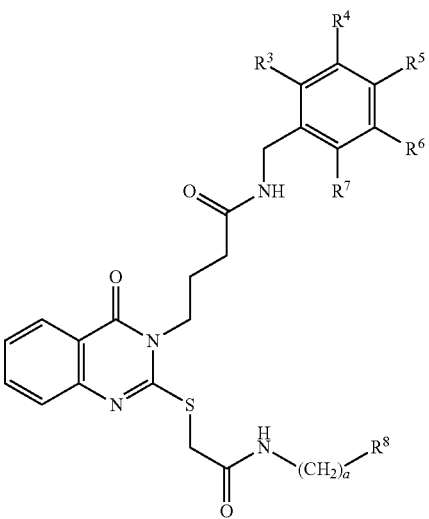

wherein each of $R^3$-$R^7$ is independently H, halogen, optionally-substituted alkyl, amino, alkoxy or hydroxy;
$R^8$ is an optionally-substituted heterocycloalkyl; and
a is 0 to 3.

Additionally disclosed herein is a method for treating frontotemporal dementia, a mitochondrial disease caused by mutations in nuclear DNA, a mitochondrial disease caused by mutations in mtDNA, or a disease of skeletal or cardiac muscle in a subject, comprising administering to the subject in need thereof, a compound, or a pharmaceutically acceptable salt thereof, of formula I:

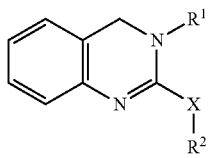

wherein $R^1$ and $R^2$ are each independently optionally-substituted alkyl, optionally-substituted aryl, amino, optionally-substituted heterocyclic, acyl, aminocarbonyl, carbonylamino, or substituted thiol; and
X is S or $CH_2$.

Also disclosed herein is a method for treating frontotemporal dementia, a mitochondrial disease caused by mutations in nuclear DNA, a mitochondrial disease caused by mutations in mtDNA, or a disease of skeletal or cardiac muscle in a subject, comprising administering to the subject in need thereof, a compound, or a pharmaceutically acceptable salt thereof, of formula II:

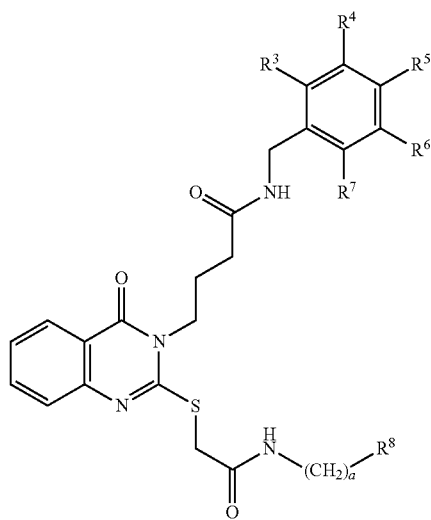

wherein each of $R^3$-$R^7$ is independently H, halogen, optionally-substituted alkyl, amino, alkoxy or hydroxy;
$R^8$ is an optionally-substituted heterocycloalkyl; and
a is 0 to 3.

The foregoing will become more apparent from the following detailed description, which proceeds with reference to the accompanying figures.

BRIEF DESCRIPTION OF THE DRAWINGS

FIGS. 1A-1E. Fbxo7 mediates Pink1 polyubiquitylation and proteasomal degradation. FIG. 1A. BEAS-2B cells were pretreated with MG132 (20 μM), leupeptin (100 μM), or diluent (control, CON) for 30 min, and then were treated with CHX (40 μg/ml) to assay protein decay. The cell lysates were obtained at the indicated time points for immunoblotting. FIG. 1B. BEAS-2B cells were nucleofected with V5-tagged Fbxo7 plasmid at indicated amounts and incubated for 48 h, the whole cell lysates were subjected to immunoblotting. FIG. 1C. BEAS-2B cells were nucleofected with 4 individual shRNAs respectively and analyzed by immunoblotting. FIG. 1D. BEAS-2B cells were nucleofected with control shRNA or Fbxo7 shRNA for 72 h, and then treated with CHX (40 gig/ml). The cells were collected at indicated time points for half-life analysis. FIG. 1E. In vitro ubiquitylation assays were performed with synthesized Pink1 combined with indicated recombinant proteins.

FIGS. 2A-2C. Fbxo7 triggers mitochondrial injury. FIGS. 2A, 2C. BEAS-2B cells were transfected with control vector or Fbxo7 plasmid for 48 h, or transfected with shRNAs for 72 h. Cells were treated with 50 μM CCCP for 5 min where indicated, and then stained with JC1 (2 μM) for additional 20 min before confocal microscopic analysis. FIG. 2B. BEAS-2B cells were nucleofected with either control vector or Fbxo7 plasmid for 48 h. The cells were then treated with or without CCCP (20 μM) for 1 h. The cells were stained with Mitosense Red and Annexin V following the manufacturer's protocol before flow cytometry analysis.

FIG. 3G. H&E staining was performed on lung samples from A. Data are an average of 5-8 mice/group. H. Mouse lung tissue from each group was homogenized and subjected to immunoblotting analysis.

FIG. 4G. H&E staining was performed on lung samples from A. Data are an average of 5-8 mice/group. FIG. 4H. Mouse lung tissue from each group was homogenized and subjected to immunoblotting analysis.

FIGS. 5A-5G. Fbxo7 FP domain small molecule inhibitor accumulates Pink1 protein. FIG. 5A. Structural analysis of the Fbxo7 FP domain. Docking study of a candidate inhibitor BC1464 within the Fbxo7-FP domain suggests hydrophilic interactions of residues GLN215, LYS235 and LYS266 with BC1464. FIG. 5B. His pull down Fbxo7 protein was captured with protein A/G beads from BEAS-2B cell lysates. Fbxo7 beads were extensively washed prior to exposure to BC1464 at indicated concentrations. TnT synthesized Pink1 protein was then incubated with drug bound Fbxo7 beads overnight, beads were washed, and proteins were eluted and subjected to immunoblotting. The relative amounts of Pink1 detected in the pull-downs was normalized to loading and quantified. FIG. 5C. BEAS-2B cells were incubated with BC1464 or the control compound BC1465 at the indicated concentrations for 16 h before immunoblotting. FIG. 5D. BEAS-2B cells were pretreated with BC1464 or BC1465 (1 μg/ml) for 16 h, and the cells were then incubated with CHX at the concentration of 40 µg/ml. The cell lysates collected at indicated time points were subjected to immunoblot analysis. FIG. 5E. H9C2 cells were incubated with BC1464 or BC1465 at indicated concentrations for 16 h. Steady-state mRNA was analyzed by quantitative real-time PCR using Pink1, Fbxo7 primers and normalized to GAPDH. FIG. 5F. PBMCs were pretreated with BC1464 at indicated concentrations for 2 h before an additional 4 h treatment with LPS (10 ng/ml). TNF secretion was measured using an ELISA. FIG. 5G. Nontargeting control (Con) or Fbxo7 siRNA (50 µg) were nucleofected into BEAS-2B cells. After incubation for 3 days, BC1464 at indicated concentrations were added for an additional 18 h. Cell lysates were subjected to immunoblot analysis.

FIG. 6A. H9C2 cells were treated with BC1464 or BC1465 (100 ng/ml) for 16 h, tBHP (100 µM) was then added for an additional 45 min incubation. Cells were stained with MitoTracker Red for 20 min before flow cytometry analysis. FIG. 6B. H9C2 cells were treated with BC1464 or BC1465 (100 ng/ml) for 16 h, and then were treated with CCCP (20 µM) for an additional 2 h. Cells were stained with JC1 (2 µM) for 20 min before confocal microscopy analysis. FIG. 6C. H9C2 cells were treated with BC1464 or BC1465 (100 ng/ml) for 16 h, with CCCP (20 µM) for an additional 2 h, and then stained with Mitosense Red and Annexin V following the manufacturer's protocol before flow cytometry analysis. Depolarized mitochondria percentage was quantified in FIG. 6D.

FIGS. 7A-7H. Fbxo7 small molecule inhibitor protects against neurotoxicity and inflammation in primary neuron and human models. FIG. 7A. Human SHSY5Y cells stably expressing PINK1-Flag were treated with the indicated amounts of BC1464 for 3 h. Cells were then incubated for 1 h in the presence of cycloheximide (10 µg/ml) before harvesting for immunoblot analysis. FIG. 7B. SHSY5Y cells were plated in a 96-well plate. After 24 h, cells were treated with the indicated concentrations of MPP+ or vehicle control (CTR) in the presence of either 5 µg/ml BC1465 or BC1464 for 24 h. Cell viability was measured using AlamarBlue fluorescence intensity. Data is the average of our independent experiments (mean±SE). FIG. 7C. Mouse E16 primary cortical neurons were plated in a 96-well plate. After 1 wk in vitro, neurons were treated with the indicated concentrations of MPP+ in the presence of either 5 µg/ml BC1465 or BC1464 for 24 h, and cell numbers measured as in B. Data is the average of four independent experiments (mean±SE). FIG. 7D-7E. Primary mouse cortical neurons were transfected with GFP at DIV7, and then treated at DIV14 with 5 µg/ml BC1465 or BC1464 prior to being challenged with the indicate concentrations of MPP+ for 24 h. Scale bar=100 µm. Neurons were assessed for morphological injury as indicated in Methods, and the average number of long, intact neuronal cell processes quantified. F. Primary fibroblasts from a control subject and two Parkinson's disease patients, one with the G2019S mutation of LRRK2 and the other with the R1441G mutation, were treated with 400 µM MPP+ for 16 h in the presence of DMSO, BC1464 or BC1465 and % cell death assessed. FIG. 7G-7H. Human lung slices were treated with BC1464 or BC1465 for 4 h at the indicated concentrations before they were challenged with LPS (100 ng/ml) for an additional 4 h. Lung slices were collected for immunoblotting G and supernatant was collected for TNF ELISA analysis in H.

FIG. 8G. H&E staining was performed on lung samples from A. Data are an average of 4-6 mice/group). FIG. 8H. Mice lung tissue from each group was homogenized and subjected to immunoblot analysis.

DETAILED DESCRIPTION

Overview

Figure 1A:
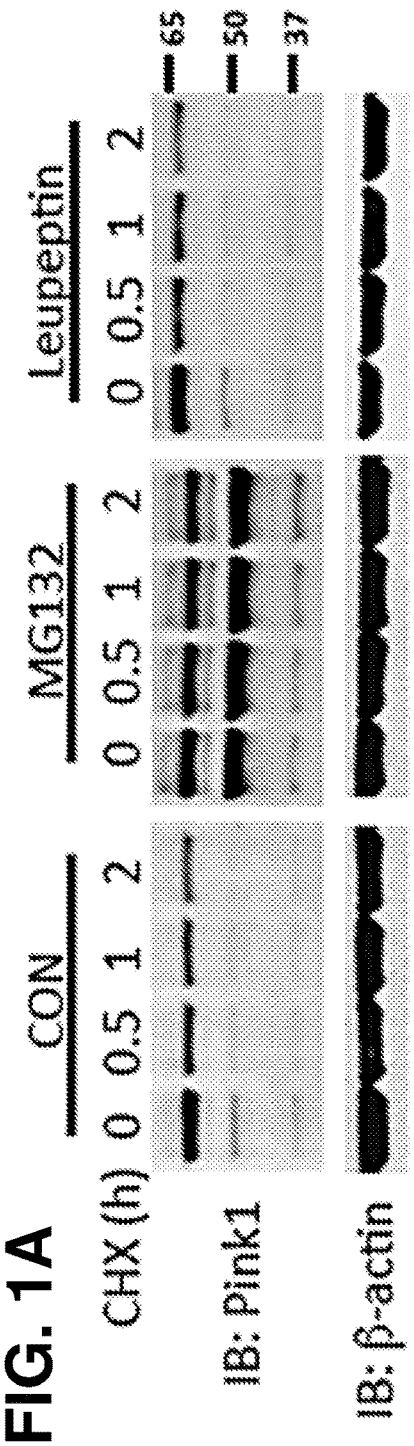

There is mounting evidence that Pink1 is critical to maintaining cellular bioenergetics and preserving mitochondrial homeostasis in a growing number of tissues. Pink1 provides an array of pro-survival, metabolic and anti-inflammatory roles, is regulated by both limited proteolysis and degradation, and mutations or loss of this protein are linked to neurodegenerative disorders and enhanced susceptibility to inflammation and pulmonary fibrosis.

These observations underscore an unmet need to identify specific molecular regulators of Pink1 degradation in cells that could lead to design and testing of therapeutic modalities to modulate Pink1 cellular concentrations. The findings here show i) that Pink1 is targeted for cellular elimination by its interaction with and site specific ubiquitylation by the SCF-Fbxo7 apparatus leading to its degradation within the proteasome, ii) that Fbxo7 is both sufficient and necessary to induce mitochondrial injury and lung inflammation, and iii) a unique first-in-class chemical entity (BC1464) that disrupts the Pink1-Fbxo7 interaction effectively lessens the severity of neurotoxicity and inflammatory injury in multiple cellular and in vivo models.

Mitochondria have long been appreciated as essential effectors of cellular processes beyond energy production. Especially in the case of cellular stress, damaged or depolarized mitochondria undergo clearance through autophagy (mitophagy), mediated by cardiolipin externalization, Pink1 and the ubiquitin E3 ligase Parkin, to recycle mitochondrial materials and maintain mitochondrial integrity and cellular balance. In addition, Pink1 plays an upstream role in maintaining mitochondrial respiratory function, membrane potential and decreasing ROS generation.

The accumulation of damaged mitochondria in Pink1-deficient systems causes an amplifying cycle involving further increases in reactive oxygen species and inefficient ATP biosynthesis, lowering the threshold for cytochrome c release and activation of apoptosis. Not only are Pink1 and Parkin mutations well described in familial recessive Parkinson's disease, but also Fbxo7 mutations have been identified in individuals with a Parkinsonian syndrome. Most notably, Fbxo7 interacts with and modulates Parkin protein turnover in Drosophila. In addition, Fbxo7 also drives inflammation through ubiquitylation and assembly of subunits associated with Parkinson's disease, such as NRAGE. Fbxo7 targets the multi-functional anti-apoptotic protein cellular inhibitor of apoptosis protein-1 for ubiquitylation and ubiquitylates hepatoma up-regulated protein for proteasome-mediated proteolysis. Thus, the possibility that therapeutic targeting of Fbxo7 might coordinately reduce abundance of several proteins involved in promoting inflammation, dendrite retraction or cell death in neurodegenerative disease is compelling.

Prior data on Pink1 protein lifespan in cells has mainly focused on the effects of global mitochondrial depolarization in preventing its degradation, an experimental manipulation that is not therapeutically tractable. Pink1 is stabilized by Bcl-2-associated athanogene family proteins (BAG) and by the molecular chaperones Hsp90 and Cdc37/p50. A proteolytically processed form of Pink1 is constitutively and rapidly degraded through the N-end rule pathway. This Pink1 fragment is ubiquitylated by the ubiquitin E3 ligases Ubr1, Ubr2 and Ubr4 for proteasomal degradation, which requires the sequential actions of Pink1 mitochondrial import, presenilin-associated rhomboid-like protease (PARL)-processing to generate a N-terminal degron, and retrotranslocation of a degradable Pink1 fragment to the cytosol where degron recognition may occur. However, mechanisms that govern the stability of the full-length Pink1 protein by E3 ligases are unclear. Our studies uncover a key function of SCFFbxo7 as an ubiquitin E3 ligase complex that targets Pink1 for its elimination in cells. Specifically, the studies unveil a unique mechanism whereby high cellular concentrations of Fbxo7 may induce mitochondrial damage and inflammation by depleting Pink1 through ubiquitylation and proteasomal degradation.

The precise mechanism(s) whereby Fbxo7 and Pink1 affect mitochondrial function, and modulate Parkinson's disease pathogenesis remains largely controversial, partly because both proteins have varied functions in different tissues depending on a specific cellular context. While Pink1 is necessary for mitophagy induced by laser damage and ionophores, it is not necessary for mitophagy induced in other models or as a result of its own deficiency. The partial protection against MPP+ observed in fibroblasts with the LRRK2-G2019S kinase gain of function mutation may relate to competing effects on autophagy, as LRRK2-G2019S drives pathological levels of autophagy. Besides regulating mitophagy, PINK1 has an important role in suppressing production of reactive oxygen species. Notably, stabilizing PINK1 levels by BC1464 treatment protected against 6-OHDA toxicity, an oxidative model of Parkinson's disease. Also, in response to gram-positive bacterial infection with *Staphylococcus aureus*, Pink1 knockout mice display decreased severity of lung injury, in contrast to findings in the current study where decreased Pink1 levels are linked to exacerbation of inflammatory lung injury due to a gram negative pathogen. This might be explained by selective recognition of cellular receptors to different pathogenic bacteria by unique signaling pathways. Specifically, Toll-like receptor TLR2 is implicated in the recognition of Gram-positive bacterial cell wall components, such as *Staphylococcus aureus* peptidoglycan, whereas TLR4 recognizes the gram-negative bacterial cell wall component LPS. Decreased Pink1 is also linked to development of aging related pulmonary fibrosis, a late stage sequelae of sterile lung inflammation. Another possibility is that there may be a tight physiological window within various cellular compartments for concentrations of Pink1 that allow for the kinase to act as a molecular switch. In this model, very high Pink1 concentrations could drive an anti-inflammatory state and promote mitophagy and degradation of mitochondria-associated Pink1. However, with prolonged stress, SCF-Fbxo7 mediated Pink1 ubiquitylation and degradation would prevent newly synthesized full-length Pink1 from repopulating residual mitochondria, leading to further disruption of mitochondrial function. Lastly, each E3 ligase theoretically targets several substrates for ubiquitylation, a modification that triggers not only proteolysis, but also signaling events, or translocation. We cannot exclude the possibility that aside from Pink1, other yet unknown substrates targeted by Fbxo7 also regulate the mitochondrial apparatus, which could either enhance or attenuate the role of Pink1 in mitochondrial quality control.

Nevertheless, the identification of an F box protein small molecule antagonist capable of restoring Pink1 concentrations in cells fulfills a void in the preclinical arena with implications for both neurodegenerative diseases and pro-inflammatory disorders.

Although our studies with BC1464 are preclinical, we were able to demonstrate ability of the compound to i) abrogate molecular interaction between Fbxo7 and Pink1, ii) increase immunoreactive content of Pink1 in cells, and iii) attenuate mitochondrial injury, cellular toxicity and inflammation triggered by potent neurotoxins and inflammatory agonists. Target validation studies depleting Fbxo7 abrogated the ability of BC1464 to further regulate Pink1 cellular concentrations. The results provide a mechanistic strategy for chemical evolution based on the backbone of the Fbxo7 docking compound that can be used to develop the pharmacodynamics and pharmacokinetic properties of a new generation of chemical entities. Our results may set the stage for more rigorous in vivo target validation and guide work that can proceed in parallel with investigative pharmacokinetic and efficacy studies in an expanded range of animal models of neurodegenerative disease and other disorders that display a fundamental defect of mitochondrial function.

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Administration" as used herein is inclusive of administration by another person to the subject or self-administration by the subject.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls"

wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C1-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, acyl, aryl, aralkyl, cycloalkyl, halogenated alkyl, or heterocycloalkyl group. For example, an "alkylamino" or "alkylated amino" refers to —NRR', wherein at least one of R or R' is an alkyl. A suitable amine or amino group is acetamido.

The term "aminoalkyl" refers to alkyl groups as defined above where at least one hydrogen atom is replaced with an amino group (e.g., —$CH_2$—$NH_2$).

"Aminocarbonyl" alone or in combination, means an amino substituted carbonyl (carbamoyl) radical, wherein the amino radical may optionally be mono- or di-substituted, such as, for example, with alkyl, aryl, acyl, aralkyl, cycloalkyl, cycloalkylalkyl, alkanoyl, alkoxycarbonyl, aralkoxycarbonyl and the like. For example, an aminocarbonyl may be represented by the formula —C(O)NRR', where R and R' independently can be, for example, a hydrogen, alkyl, alkenyl, alkynyl, acyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

A "carbonylamino" group may be —N(R)—C(O)—R (wherein each R is independently a substitution group such as, for example, alkyl, alkenyl, alkynyl, acyl, aryl, aralkyl, cycloalkyl, halogenated alkyl, or heterocycloalkyl group, or H). A suitable carbonylamino group is acetamido.

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

Small organic molecule: An organic molecule with a molecular weight of about 1000 daltons or less (for example about 900 daltons or less, about 800 daltons or less, about 700 daltons or less, about 600 daltons or less, about 500 daltons or less, about 400 daltons or less, about 300 daltons or less, about 200 daltons or less, or about 100 daltons or less). In some examples, a small organic molecule has a molecular weight of about 100-1000 daltons, about 200-900 daltons, about 300-700 daltons, about 200-500 daltons, or about 400-700 daltons.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

The term "substituted thiol" refers to a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C=C, C=N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}$F, etc.

Compounds

Disclosed herein are compounds, and pharmaceutically acceptable salts thereof, of formula I:

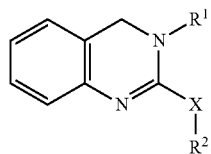

wherein $R^1$ and $R^2$ are each independently optionally-substituted alkyl, optionally-substituted aryl, amino, optionally-substituted heterocyclic, acyl, aminocarbonyl, carbonylamino, or substituted thiol; and X is S or $CH_2$; provided that the compound is not

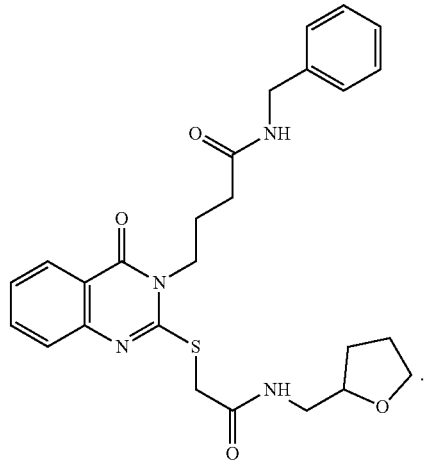 [SMILES: O=C(CCCn1c(SCC(=O)NCC2CCCO2)nc2ccccc2c1=O)NCc1ccccc1]

In certain embodiments, $R^1$ and $R^2$ are each independently aralkyl, aminoalkyl, thioalkyl, or heterocyclic-substituted alkyl.

In certain embodiments, X is S.

Also disclosed herein are compounds, and pharmaceutically acceptable salts thereof, of formula II:

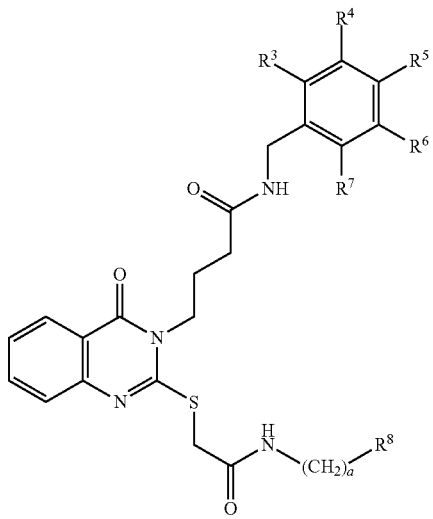

wherein each of $R^3$-$R^7$ is independently H, halogen, optionally-substituted alkyl, amino, alkoxy or hydroxy;

$R^8$ is an optionally-substituted heterocycloalkyl; and a is 0 to 3; provided that the compound is not

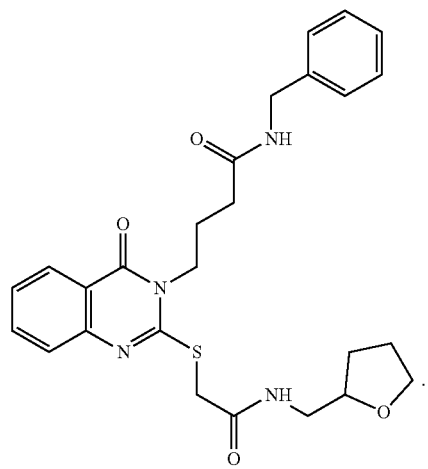 [SMILES: O=C(CCCn1c(SCC(=O)NCC2CCCO2)nc2ccccc2c1=O)NCc1ccccc1]

In certain embodiments, at least one of $R^3$-$R^7$ may be unsubstituted alkyl or substituted alkyl, particularly aminoalkyl (e.g. —$(CH_2)_b$—$NR^9R^{10}$, wherein $R^9$ and $R^{10}$ are each independently H or alkyl (particularly ($C_1$-$C_6$)alkyl) and b is 1 to 5).

In certain embodiments, at least one of $R^3$-$R^7$ may be amino, particularly —$NH_2$ or alkylamino (e.g., —$NR^{11}R^{12}$, wherein $R^{11}$ and $R^{12}$ are each independently H or alkyl (particularly ($C_1$-$C_6$)alkyl)).

In certain embodiments, at least one of $R^3$-$R^7$ may be alkoxy, particularly ($C_1$-$C_8$)alkoxy, and more particularly methoxy.

In certain embodiments, $R^5$ is not H.
In certain embodiments, $R^5$ is alkoxy.
In certain embodiments, $R^5$ is alkylamino.
In certain embodiments, at least two of $R^3$-$R^7$ are halogen.
In certain embodiments, at least one of $R^3$-$R^7$ is not H.
In certain embodiments, each of $R^3$-$R^7$ is H.
In certain embodiments, $R^8$ is a 5-membered heterocycloalkyl or a 6-membered heterocycloalkyl.

In certain embodiments, $R^8$ is a heterocycloalkyl that includes at least one oxygen heteroatom (i.e., an O-heterocycloalkyl). Illustrative O-heterocycloalkyls include oxetanyl, dioxetanyl, oxolanyl, dioxolanyl, oxanyl and dioxanyl. Particularly preferred O-heterocycloalkyl are oxolanyl and oxanyl. For example, in certain embodiments, $R^6$ is:

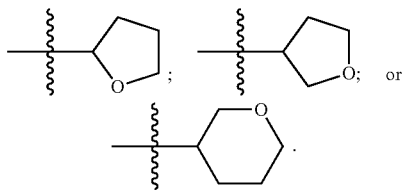

In certain embodiments, a is 1.
In certain embodiments, a is 2.
In certain embodiments, a is 3.

The compounds disclosed herein may be synthesized, for example, following the scheme below.

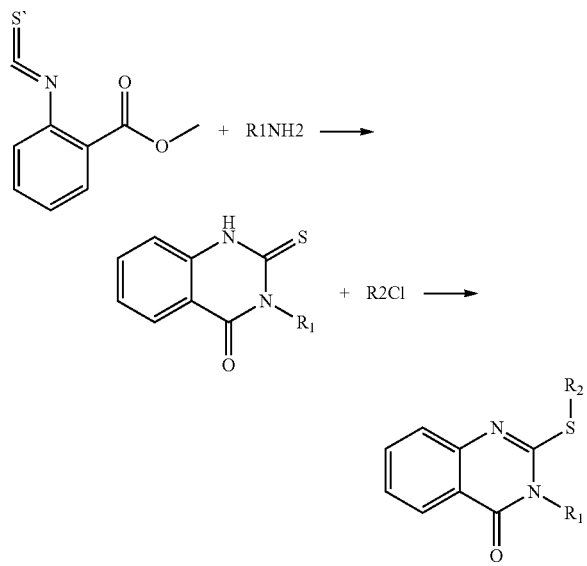

Pharmaceutical Compositions and Methods of Use

In certain embodiments, the compounds described herein may be useful for treating neurodegenerative diseases or inflammatory disorders, particularly Fbxo7-mediated diseases or disorders. For example, the compounds may i) abrogate molecular interaction between Fbxo7 and Pink1, ii) increase immunoreactive content of Pink1 in cells, and iii) attenuate mitochondrial injury, cellular toxicity and inflammation triggered by potent neurotoxins and inflammatory agonists.

Illustrative neurodegenerative diseases include Parkinson's disease, Alzheimer's disease and other dementias, Tauopathies, Amyotrophic lateral sclerosis (ALS; also known as motor neurone disease (MND) or Lou Gehrig's disease), Huntington's disease (HD), stroke, Aging neurodegeneration, Prion disease, Spinocerebellar ataxia (SCA), Spinal muscular atrophy (SMA), Alexander disease, Alper's disease, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Pelizaeus-Merzbacher Disease, Pick's disease, Primary lateral sclerosis, Refsum's disease, Sandhoff disease, Schilder's disease, Sub-Acute Combined Degeneration of the Cord Secondary to Pernicious Anaemia, Schizophrenia, Spielmeyer-Vogt-Sjogren-Batten disease (also known as Batten disease), Steele-Richardson-Olszewski disease and Tabes dorsalis, dominant optical atrophy (DOA).

Illustrative inflammatory disorders include acute and chronic inflammation disorders such as asthma, chronic obstructive lung disease, pulmonary fibrosis, pneumonitis (including hypersensitivity pneumonitis and radiation pneumonitis), pneumonia, cystic fibrosis, psoriasis, arthritis/rheumatoid arthritis, rhinitis, pharyngitis, cystitis, prostatitis, dermatitis, allergy including hay fever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (Crohn's disease, ulcerative colitis)/colitis, sepsis, vasculitis, bursitis, connective tissue disease, autoimmune diseases such as systemic lupus erythematosis (SLE), polymyalgia rheumatica, scleroderma, Wegener's granulomatosis, temporal arteritis, vasculitis, cryoglobulinemia, and multiple sclerosis, viral or influenza-induced inflammation, or edema.

In certain embodiments, the compounds described herein may be useful for treating pulmonary diseases, such as lung diseases. The lung is the site of a wide variety of diseases and pathological conditions. Illustrative pulmonary diseases include pulmonary fibrosis, chronic obstructive pulmonary disease (COPD), asthma, cystic fibrosis, acute lung injury (ALI), acute respiratory distress syndrome, pulmonary hypertension, lung cancer, pulmonary manifestations of cystic fibrosis, acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome.

In certain embodiments, the compounds described herein may be useful for treating diseases or disorders in which mitochondrial dysfunction or oxidative stress are implicated. For example, compounds that upregulates Pink1 may be useful in treating diseases in which mitochondrial quality control is implicated. Illustrative diseases include frontotemporal dementia, mitochondrial diseases caused by mutations in nuclear DNA, mitochondrial diseases caused by mutations in mtDNA, and diseases of skeletal or cardiac muscle.

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

In some embodiments, one or more of the disclosed compounds are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

EXAMPLES

Cell Culture and Transfection.

Murine lung epithelial (MLE12) cells (ATCC) and BEAS-2B cells were cultured with HITES medium (DMEM:F12 supplemented with insulin, transferrin, hydrocortisone, β-estradiol and glutamine) containing 10% fetal bovine serum (FBS) and antibiotics as described previously. H9C2 cells were cultured in DMEM medium supplemented with 10% FBS and antibiotics. For half-life studies, cells were treated with cycloheximide (40 μg/ml) in blank medium and collected at different time points. Cells lysates were prepared by brief sonication in 150 mM NaCl, 50 mM Tris, 1.0 mM EDTA, 2 mM dithiothreitol, 0.025% sodium azide, and 1 mM phenylmethylsulfonyl fluoride (RIPA buffer) at 4° C. All plasmids were delivered into cells using nucleofection following manufacturer's protocols. All plasmid constructs were generated using PCR-based strategies with appropriate primers; point mutants were generated using site-directed mutagenesis kit (50). SH-SY5Y cells (ATCC, Manassas, Va.) were maintained in antibiotic-free Dulbecco's modified Eagles's Medium (DMEM; BioWhittaker, Walkersville, Md.) supplemented with 10% fetal bovine serum (Mediatech Inc, Manassas, Va.), 2 mM L-glutamine and 10 mM HEPES in humidified incubator at 37° C. and 5% CO2. Timed pregnant female C57BL/6 mice were purchased from Charles Rivers Laboratories. Procedures for the derivation of primary neuron cultures were approved by the University of Pittsburgh Institutional Animal Care and Use Committee. Primary E16 cortical neurons were plated at 150,000-200,000 cells/cm2 in LabTek II coverglass chamber slides or tissue culture plates coated with poly-L-lysine (0.1 mg/ml), and maintained in antibiotic-free Neurobasal medium supplemented with 2% B27 and 2 mM glutamax (Gibco, Bethesda, Md.). SHSY5Y cells and cortical neurons in 96-well plates were treated with the indicated concentrations of MPP+ and 5 μg/ml of either BC1464 or BC1465 (structures shown below).

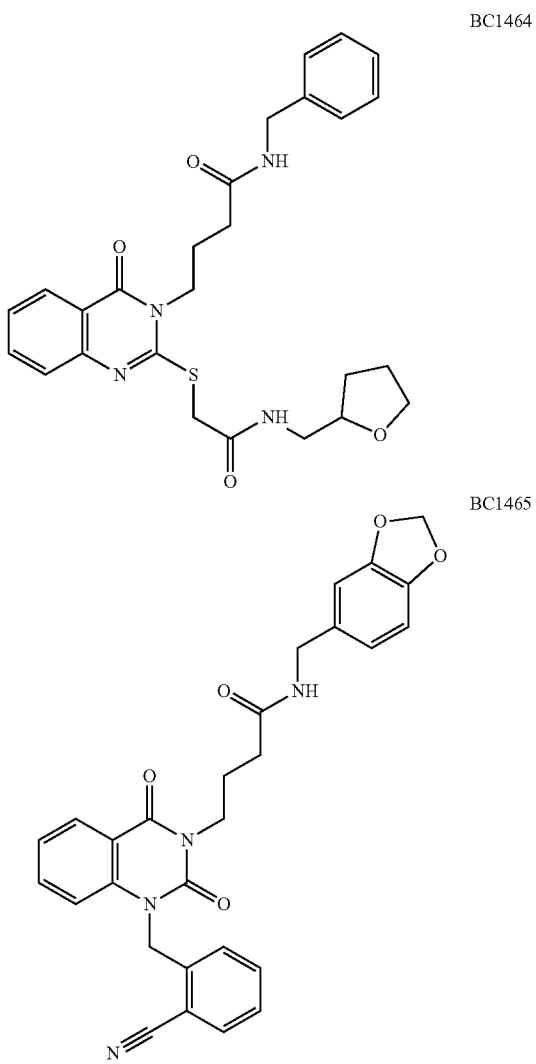

After 24 h, cell viability was analyzed using the AlamarBlue® Assay according to the manufacturer's instructions (Bio-Rad Laboratories, Hercules, Calif.). Primary fibroblasts were purchased from the NINDS Human Cell and Data Repository at Rutgers University (RUCDR Infinite Biologics). Fibroblasts were incubated with MPP+(400 μM) or 6-OHDA (300 μM) for 19 h. For morphological assessments, cortical neurons were transfected with IRES-GFP at DIV7, allowed to mature to DIV14, and then treated with 5 ng/mL of BC1464 or BC1465 4 h prior to addition of MPP+. After 24 h, cultures were analyzed for propidium iodide exclusion or processed for fluorescence imaging.

Reagents.

The pcDNA3.1D/V5-His-TOPO cloning kit, V5 antibody and *Escherichia coli* Top 10 One-Shot-competent cells were from Invitrogen (Carlsbad, Calif.). Leupeptin, β-actin mouse monoclonal antibody, 1-methyl-4-phenylpyridinium (MPP+), and carbonyl cyanide m-chlorophenylhydrazone (CCCP) were from Sigma (St. Louis, Mo.). MG-132 was from UBPBio (Aurora, Colo.). Protease inhibitor tablets and Supersignal West Femto chemiluminescent substrate were from Thermo Scientific (Rockford, Ill.). The Fbxo7 cDNA, Pink1 cDNA, scrambled shRNA, human and mouse Fbxo7 shRNAs were from OpenBiosystems (Huntsville, Ala.). Nucleofector transfection kits were from Amaxa (Gaithersburg, Md.). QuikChange site-directed mutagenesis kits were from Agilent (Santa Clara, Calif.). Immobilized protein A/G beads were from Pierce. Pink1 rabbit antibody was from Novus (Littleton, Colo.). Purified Cul1, Rbx1, and Skp1 were from Abnova (Taipei, Taiwan). Purified ubiquitin, E1, E2, and ubiquitin aldehyde were from Enzo Life Sciences (Farmingdale, N.Y.). Cycloheximide was from Calbiochem (La Jolla, Calif.). Fbxo7 rabbit antibody was from Aviva Systems Biology (San Diego, Calif.). TNT quick-coupled transcription/translation systems were from Promega (Madison, Wis.). The RNA purification kit was from Qiagen (Hilden, Germany). A real-time quantitative PCR kit was from Bio-Rad (Hercules, Calif.).

Mass Spectrometry-GFP IP products from HEK293 cells expressing either EGFPc-1 or WT-PINK1-GFP, isolated using the gMACS Epitope Tag Protein Isolation Kit (Miltenyi Biotec, Bergisch Gladbach, Germany), were electrophoresed into a stacking gel.

Resulting gel bands were excised, destained in 100 mM ammonium bicarbonate, reduced in 5 mM DTT, and alkylated in 15 mM iodoacetamide as previously described. Gel spots were washed in 50% acetonitrile/100 mM AmBic and incubated overnight in 0.05 μg/μL trypsin in 100 mM Ambic at a 1:100 enzyme to protein ratio. Digested peptides were extracted in 60% acetonitrile/0.1% trifluoroacetic acid before being lyophilized and resuspended in 5% formic acid. An EASY-nLC II liquid chromatography system was used to separate peptides. High-resolution peptide precursor measurements were made in the Orbitrap (R=60,000 at 400 m/z) and low resolution peptide fragment ion spectra were collected by collision-induced dissociation in the dual-linear ion trap of an Orbitrap Elite Mass Spectrometer. Data was searched using SEQUEST against a Uniprot-derived human protein database (downloaded Jan. 17, 2011) amended with an entry for GFP. Fold-change (Log 2) ratios were calculated following addition of 0.5 to summed peptide spectral matches (PSMs) for corresponding protein identifications to enable comparative analyses of "presence-absence" scenarios.

Mutants—

All Fbxo7 mutant constructs were generated by site-directed mutagenesis using the Stratagene Quick-change kit (San Diego, Calif.).

Flow Cytometry—

Transfected cells were incubated with MitoTracker Red (50 nM) for 15 min following the protocols of the manufacturer (Invitrogen). Cells were washed with medium four times before harvesting with trypsin digestion. Cell suspensions were then analyzed with an AccuriC6 system with De Novo software. MitoTracker staining was measured by flow cytometry FL1 (FITC; excitation wavelength, 488 nm; emission wavelength, 530 nm) and FL3 (MitoTracker Red; excitation wavelength, 488 nm; emission wavelength, 610 nm). The enclosed areas represent the percentage of defective mitochondria.

Immunoblotting and Immunoprecipitation.

Whole cell extracts (normalized to total protein concentration) were subjected to SDS-PAGE, electrotransferred to membranes, and immunoblotted. For immunoprecipitation, 1 mg of cell lysates (in PBS with 0.5% Triton X-100 plus protease inhibitors) were incubated with 2 gig of V5 mouse antibodies for 3-4 h at 4° C., followed by addition of 30 μl of protein A/G-agarose for an additional 1 h at 4° C. The precipitated complex was washed three times with 0.5% Triton X-100 in PBS and analyzed by immunoblotting with an enhanced ECL system.

In Vitro Ubiquitylation Assays.

The ubiquitylation of wild-type or lysine mutant Pink1-V5 was performed in a volume of 20 μl containing 50 mM Tris (pH 7.6), 5 mM MgCl2, 0.6 mM DTT, 400 μM MG132, 2 mM ATP, 50 nM E1, 0.5 μM UbcH5, 0.5 μM UbcH7, 2 μM ubiquitin, 1 μM ubiquitin aldehyde, 20 nM Cul1, 20 nM Rbx1, 20 nM Skp1, in vitro synthesized Pink1-HA (WT or mutant), and Fbxo7 within the TNT-coupled reticulocyte lysate system. Reaction products were examined for HA immunoblotting.

PA103 Infection.

PA103 inoculums were freshly prepared prior to experiments using frozen stocks of *P. aeruginosa* (ATCC strain 29213, frozen at midlog phase; optical density 625=0.8). *P. aeruginosa* was maintained in tryptic soy broth minimal agar. Cultures were plated and grown overnight from frozen stock. Overnight plate cultures were then inoculated in tryptic soy broth and grown by rotary shaking at 37° C. to log phase. Cells were then infected with *P. aeruginosa* at multiplicity of infection (moi)=10, 50, or 100 for 1, 2, or 16 hr.

Coimmunoprecipitation.

500 μg of total protein from cell lysates was precleared with 20 μl of protein A/G beads for 1 hr at 4° C. 2 μg of primary antibody was added to TNT synthesized Pink1 for 18 hr incubation at 4° C. 20 μl of protein A/G beads were added for an additional 6 hr of incubation. Beads were slowly centrifuged and washed five times using 50 mM HEPES, 150 mM NaCl, 0.5 mM EGTA, 50 mM NaF, 10 mM Na3VO4, 1 mM phenylmethylsulfonyl fluoride, 20 μM leupeptin, and 1% (v/v) Triton X-100 (radio-immunoprecipitation assay) buffer, as described. The beads were heated at 100° C. for 5 min with 80 μl of protein sample buffer prior to SDS-PAGE and immunoblotting.

Microscopy and Immunostaining.

Microscopy work was performed using a Nikon A1 confocal microscope with a 60×oil objective. The microscope was equipped with Ti Perfect Focus system and Tokai Hit live cell chamber providing a humidified atmosphere at 37° C. with 5% CO2. Nucleofected cells (2×105) were plated at 70% confluence on 35 mm MatTek glass bottom culture dishes, treated with or without CCCP, and then labeled with either MitoTracker Red (50 nM) or JC1 (2 μM) for additional 20 min. Image analysis was performed by Nikon NIS-element and ImageJ software. Pseudocolor green was used for optimal resolution of mitochondria MitoTracker image display. Primary neurons were fixed in 2% paraformaldehyde at room temperature for 20 min, washed 3× in PBS, permeabilized with 0.5% triton-X 100× 10 min, and washed 4×. After 1 h in SuperBlock and washing 3× in PBS with 0.1% Tween-20, neurons were incubated with rabbit anti-GFP at 1:1000 for 1 h, washed 4× and incubated with Alexa 488 conjugated secondary antibody at 1:500 for 1 h. Morphological injury was assessed by quantifying the numbers of intact neurites per neuron that exceeded a Sholl radius of 50 μm.

Animal Studies.

Male C57LB/6 mice (purchased from Jackson Laboratories) were acclimated at the University of Pittsburgh Animal Care Facility and maintained according to all federal and institutional animal care guidelines and under a University of Pittsburgh Institutional Animal Care and Use Committee-approved protocol. Mice were deeply anesthetized with ketamine (80-100 mg/kg of body weight, intraperitoneally [i.p.]) and xylazine (10 mg/kg, i.p.), and then the larynx was well visualized under a fiber optic light source before endotracheal intubation with a 3/400 24-gauge plastic catheter. Replication-deficient lentivirus (Lenti) alone or Lenti-Fbxo7, Lenti-shRNA control or Lenti-shRNA Fbxo7 (108 plaque-forming units in 50 µl of PBS) was instilled i.t. on day 1, after which animals were allowed to recover for 7 days before bacterial infection.

Human Lung Explants—

Donor human lungs not accepted for transplant were obtained through the University of Pittsburgh Committee for Oversight of Research and Clinical Training Involving Decedents (CORID). Donor medical records were de-identified and IRB approval is not required to access these tissues. Organs were considered appropriate for study if there was no evidence of parenchymal lung disease, gas exchange was within normal limits prior to harvest, and organs could be processed with less than 6 h cold ischemic time. Localized lesions (e.g. solitary nodules) were avoided during tissue selection. Single lung segments were dissected and warmed in a weighted plastic bag in a 37° C. water bath for 30 min. 2% low melting point agarose in PBS (Invitrogen Ultrapure) is also maintained at 37° C. The lung segments were filled with agarose by instillation into airways via syringe with 18 gauge cannula and inspected for appropriate expansion, followed by airway clamping. Tissue was placed in a bag and submerged in ice for 30 min or until the agarose had set. Tissue was cut to block size (2 cm×1 cm×1 cm) and sliced in ice cold saline with a vibratome (Leica VT 1200) at slice thickness of 300 µm. Uniform slices were sectioned into 1 cm×1 cm sections and cultured in RPMI containing Pen/Strep and Amphotericin B without serum in 12 well dishes at 37° C. in a tissue incubator with 5% CO2. Medium was changed after 2 h and experiments performed in 1 ml media after overnight incubation. Slices were treated with the indicated concentrations of test compounds and simultaneously exposed to 50 ng/ml LPS for 4 h before homogenization and resuspension in lysis buffer.

Statistics—

Statistical analysis was performed with an analysis of variance or unpaired Student's t test, with $p<0.05$ indicative of significance.

Figure 1C:
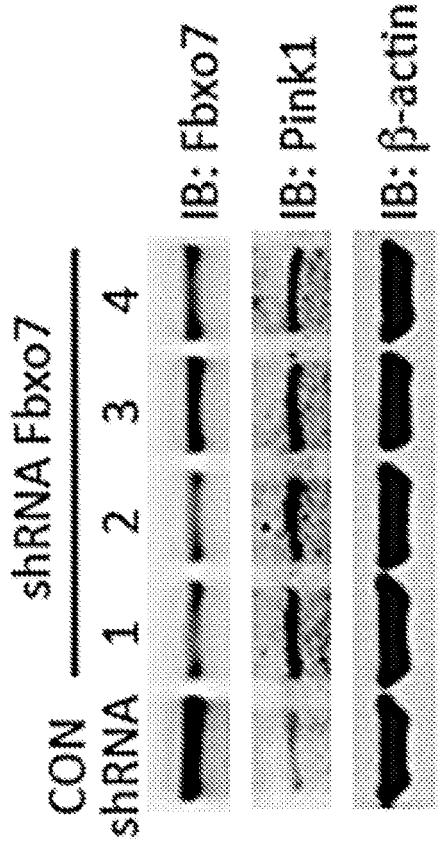
Figure 1B:
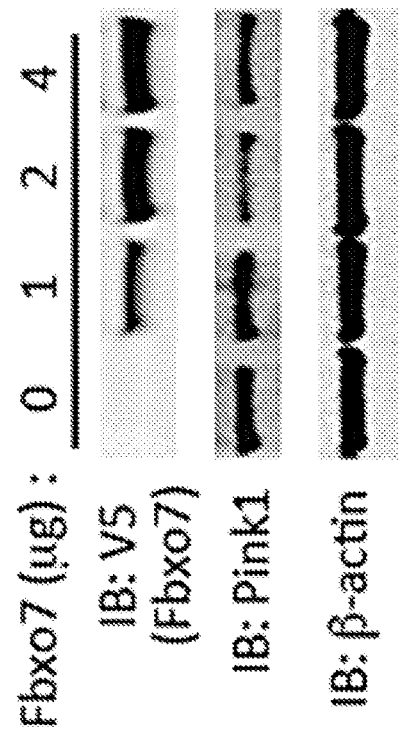

Pink1 undergoes rapid proteolysis in cells, and the cleaved Pink1 fragment may be degraded through the N-end rule pathway. To test if full length Pink1 is subjected to ubiquitin mediated degradation, we evaluated the ability of proteasomal or lysosomal inhibitors to regulate stability of the kinase. Both full-length and a fragment of Pink1 undergo rapid degradation when protein synthesis is blocked by the addition of the protein biosynthesis inhibitor cycloheximide (CHX)(FIG. 1A). Moreover, addition of the proteasome inhibitor MG132 accumulated not only the Pink1 fragment, but also full length Pink1. On the contrary, addition of a lysosomal inhibitor leupeptin to the culture medium had little impact on basal Pink1 turnover. F-box proteins recognize and recruit substrates to an ubiquitin E3 ligase catalytic core for polyubiquitylation. To examine if a F-box protein mediates Pink1 protein degradation, we screened Pink1 levels after ectopic expression of plasmids encoding individual F-box proteins from a library. F-box proteins were overexpressed in human bronchial epithelial cells, and endogenous Pink1 protein levels were compared among transfected cells expressing different F-box proteins). Full-length Pink1 protein levels remained the lowest in Fbxo7 overexpressed cells, compared to levels in cells of other overexpressed F-box plasmids. In separate studies using Pink1 as a bait for IP-mass-spectrometry, we identified Fbxo7 as a Pink1 binding partner (Table 1). We overexpressed Fbxo7 in a dose-dependent manner and detected decreased Pink1 protein levels with increasing amounts of Fbxo7 plasmid expression (FIG. 1B). Fbxo7 knockdown screening confirmed that decreased Fbxo7 led to accumulation of endogenous Pink1 protein (FIG. 1C). In FIG. 1D, we examined Pink1 half-life with effective knockdown of Fbxo7 and observed that Fbxo7 deficiency extends Pink1 lifespan in cells. Further, in vitro ubiquitylation assays confirmed that Fbxo7 enhances the Pink1 polyubiquitylation (FIG. 1E). To identify the ubiquitin acceptor site within Pink1, we constructed a series of single lysine to arginine (K-R) mutants with a V5 tag and measured protein turnover after cellular expression of the plasmids. However, none of the single point mutants slowed down the degradation of Pink1. We next analyzed the protein structure provided by the PDB database, which predicted three highly-exposed juxtaposed lysine sites (K520, K523 and K526). Cellular expression of double lysine mutants compared with wild type and single point lysine mutants revealed that the double Pink1 mutants showed greater stability. Further studies revealed that expression of a triple mutant of Pink1(K520R, K523R, K526R) resulted in an optimally extended t ½ after treatment of cells with CHX compared to wild-type Pink1. Thus, SCF-Fbxo7 targets Pink1 for multi-ubiquitylation and proteasomal degradation.

Figure 2B:
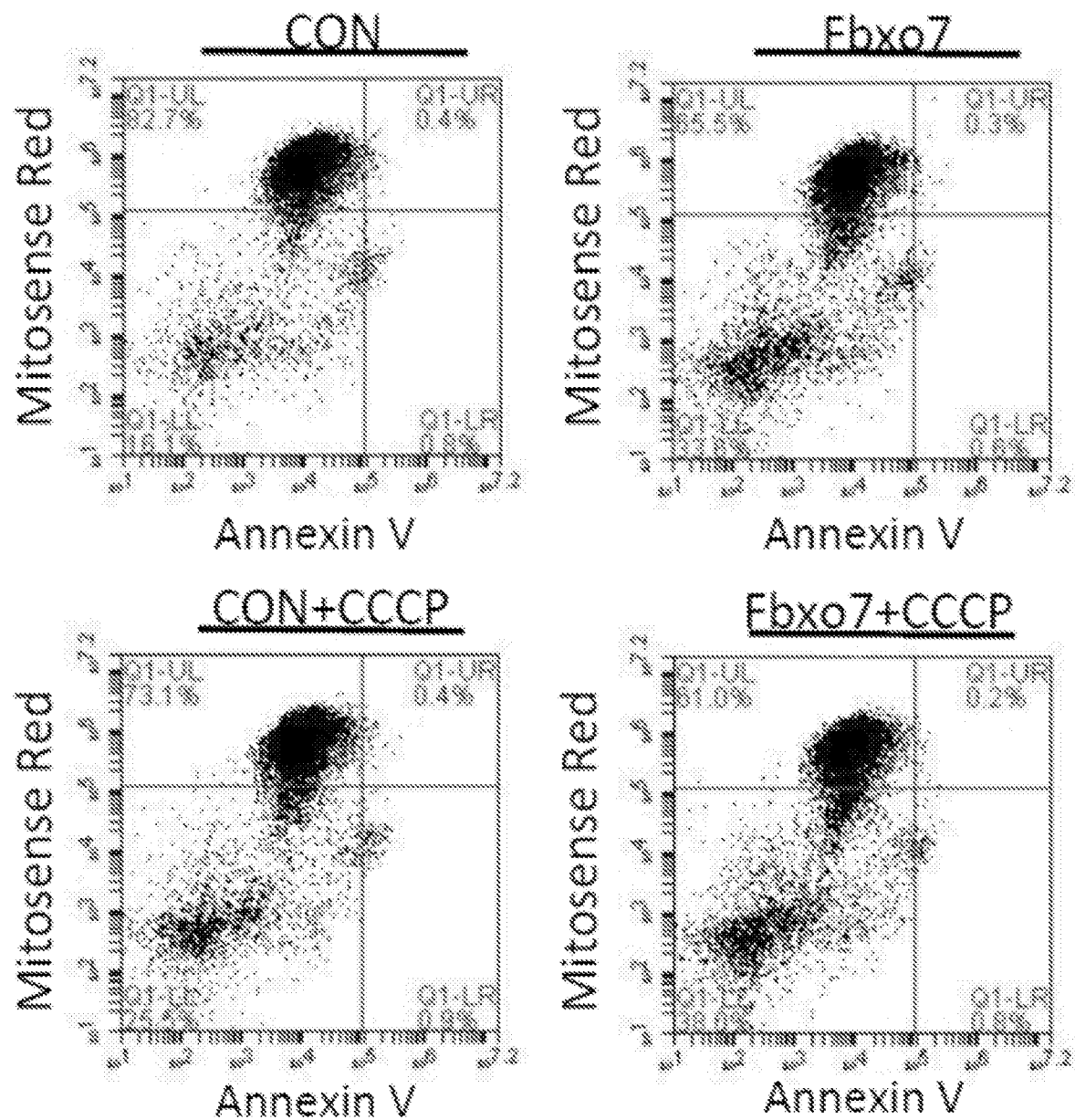
Figure 2C:
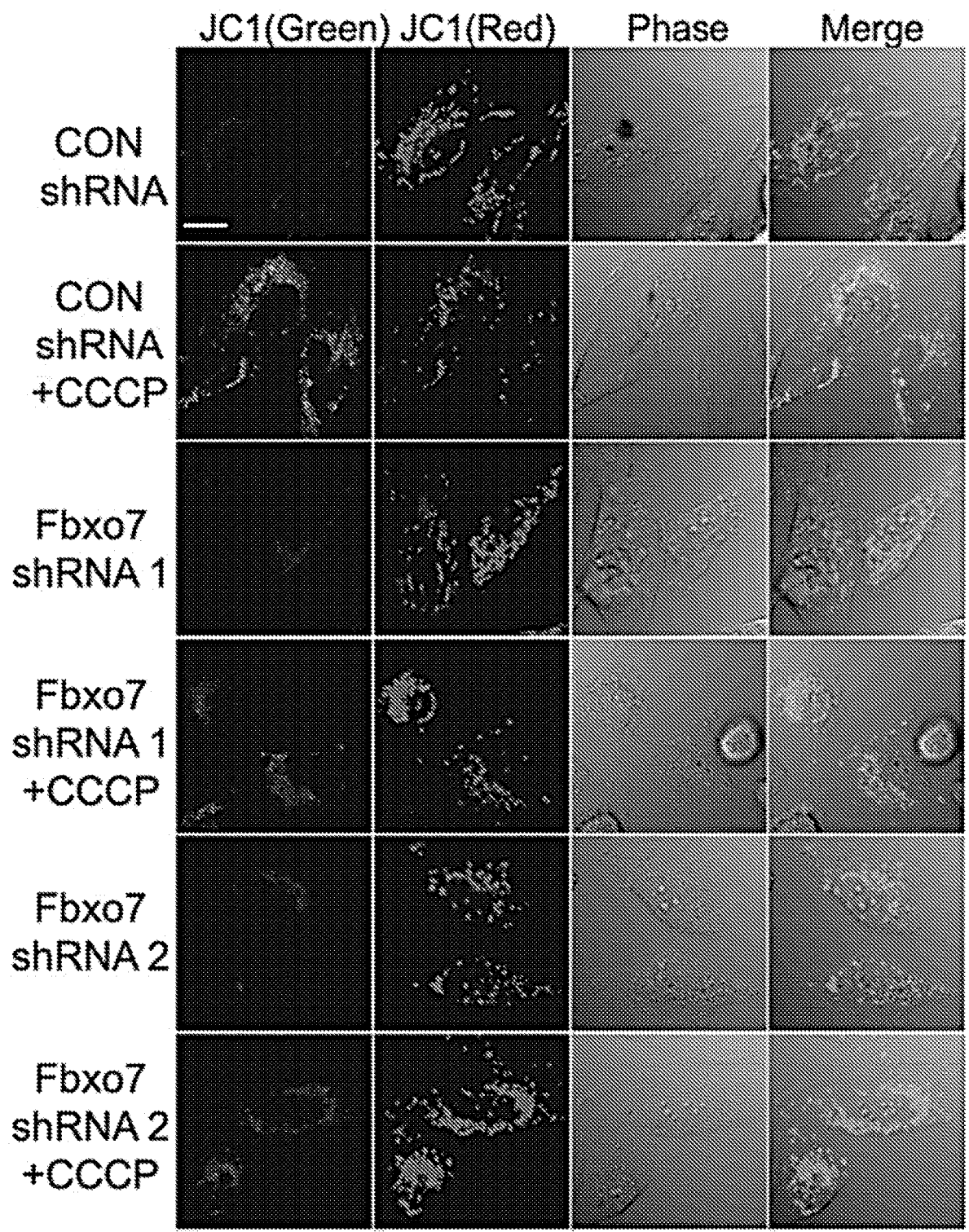

We next examined the role of Fbxo7 on mitochondrial homeostasis given that Pink1 is essential in regulating mitochondrial function. We monitored the mitochondrial membrane potential ($\Delta\Psi$) in Fbxo7 overexpressed cells using JC1. JC1 dye displays potential-dependent accumulation in mitochondria, indicated by a fluorescence emission shift from green (~529 nm) to red (~590 nm). Thus, mitochondrial depolarization is indicated by the decrease in red/green fluorescence ratio, as shown with the positive control ionophore carbonyl cyanide m-chlorophenyl hydrazine (CCCP). Similar to effects previously reported in Pink1 knockout neurons and cells, we found that overexpression of Fbxo7 alone impairs the mitochondrial membrane potential (FIG. 2A). MitoSense Red (1,1',3,3,3',3'-hexamethylindodicarbocyanine iodide) is a fluorescent cationic dye that accumulates in the mitochondria and is responsive to mitochondrial potential changes. MitoSense Red is excitable by a red laser and fluoresces maximally at 650 nm. Cells with an intact mitochondrial membrane potential demonstrate high red fluorescence, while cells with an impaired mitochondrial membrane potential display lower red fluorescence. We employed Mitosense Red combined with flow cytometry to further evaluate mitochondrial damage in Fbxo7 overexpressed cells. Compared to cells transfected with control plasmid, overexpression of Fbxo7 increased the amount of depolarized mitochondria from 16.1% to 33.6% (FIG. 2B). Fbxo7 overexpression with CCCP treatment increased numbers of damaged mitochondria from 25.5% to 38%, compared to CCCP alone, suggesting that Fbxo7 exerts an additive effect on mitochondrial injury induced by CCCP. However, Fbxo7 knockdown (FIG. 2C) largely protected mitochondria from CCCP induced injury.

Figure 3A:
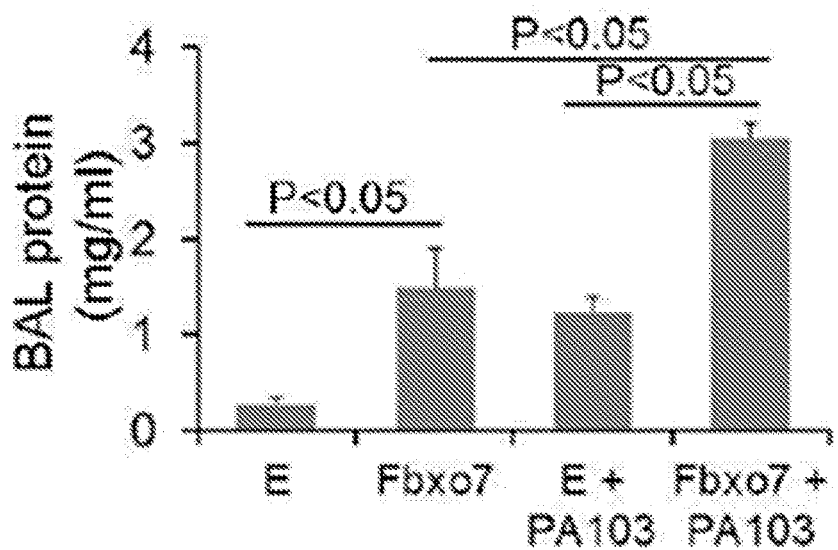
FIGS. 3A-3H. Fbxo7 induces experimental lung injury with loss of PINK1. C57BL/6J mice were administered i.t. with Lenti-control or Lenti-Fbxo7 (108 PFU/mouse) for 144 h, and 5-8 mice/group were then inoculated with PA103 (104 PFU/mouse) for 18 h. Mice were euthanized and lungs were lavaged with saline, harvested, and then homogenized. Bronchoalveolar lavage protein, cell count, bacteria loads and cytokine secretion were measured in (FIGS. 3A-3F).
Figure 3B:
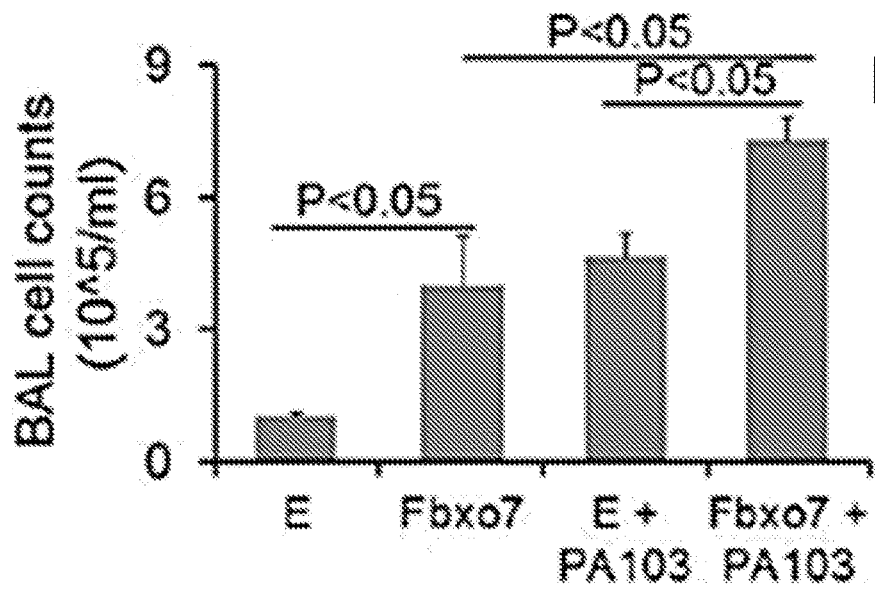
Figure 3C:
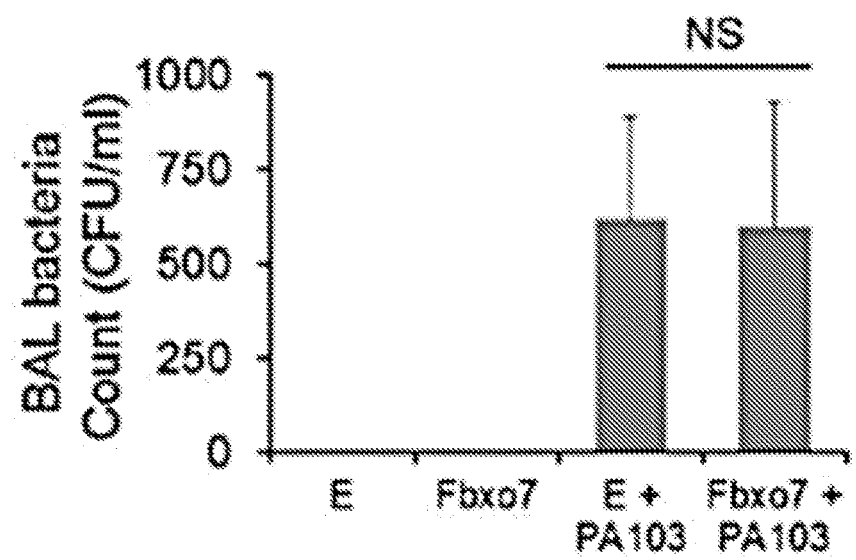
Figure 3D:
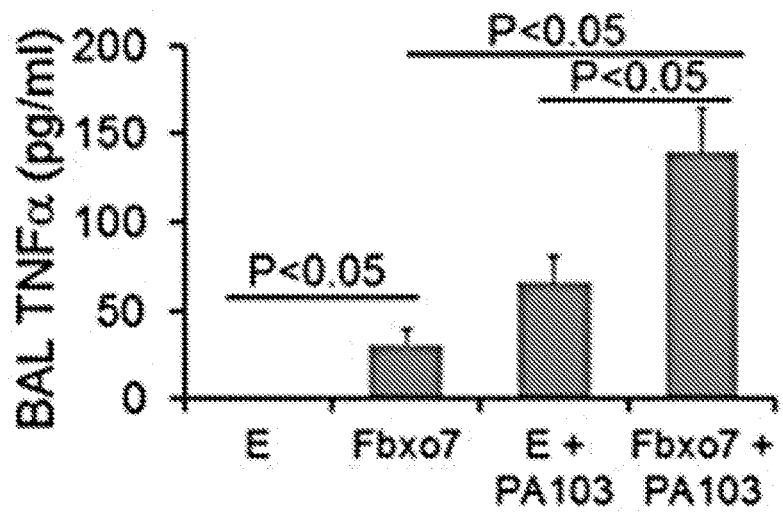
Figure 3E:
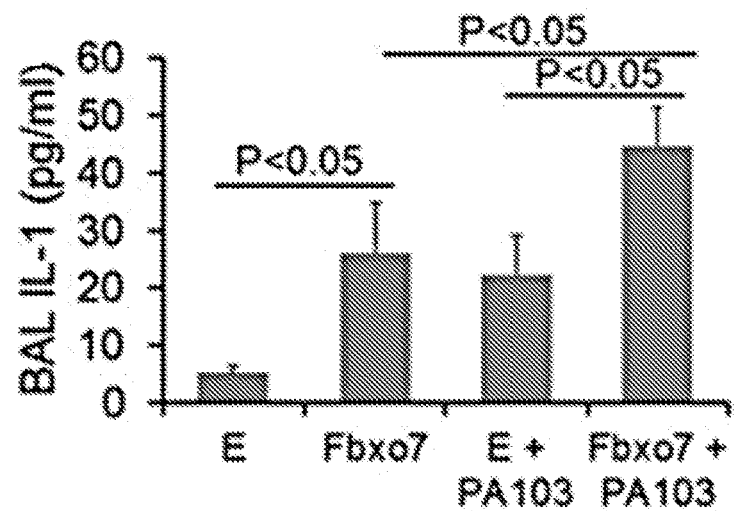
Figure 3F:
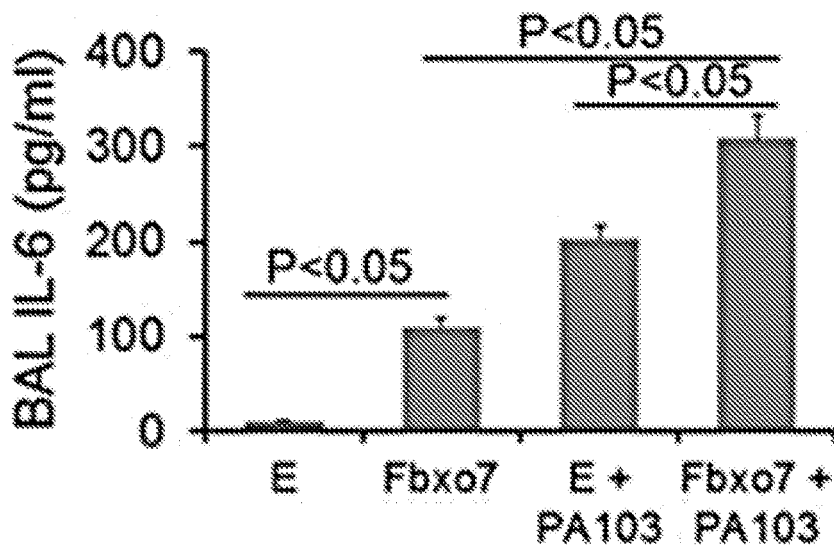
Figure 3G:
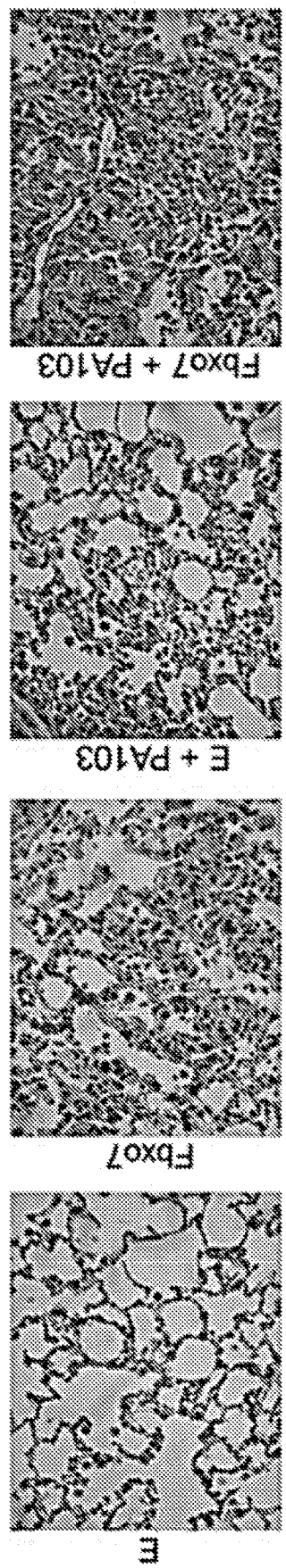
Figure 3H:
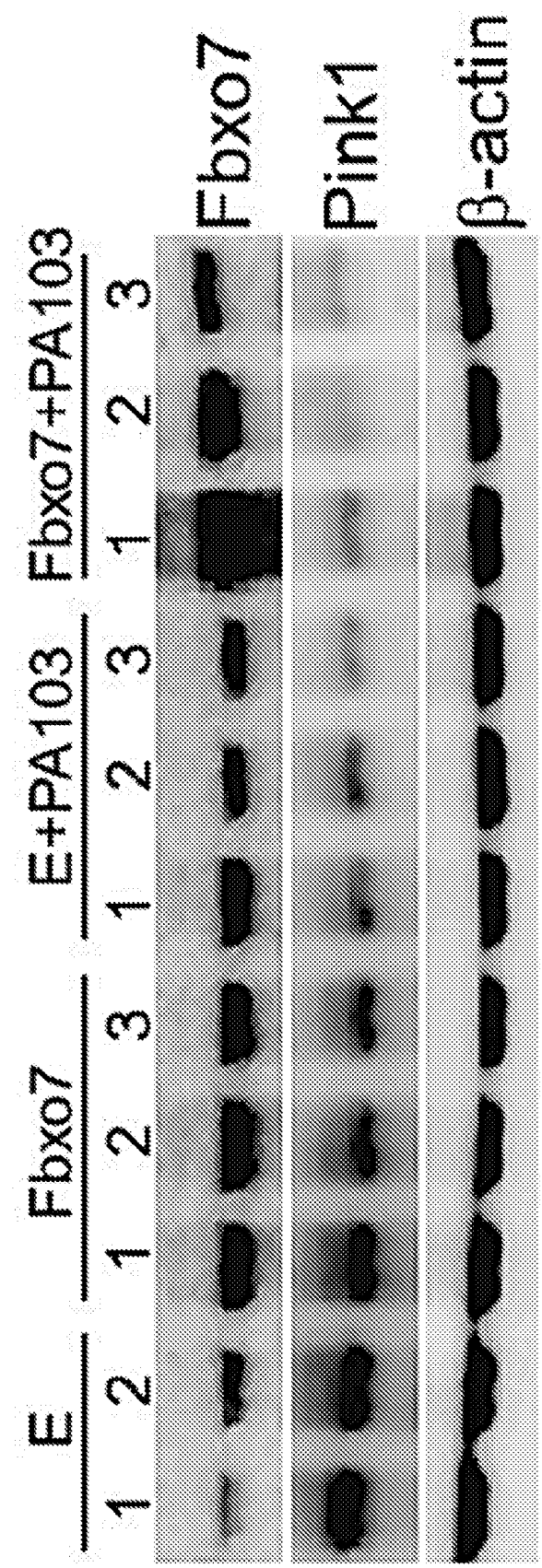

As a more biologically relevant injury model, we examined effects of Fbxo7 on mitochondrial and lung injury, given the newly described anti-inflammatory role of Pink1 and its identification as a substrate for SCF-Fbxo7 degradation. First we established that the gram-negative bacterial component, lipopolysaccharide (LPS) increased Fbxo7 mass and decreased Pink1 protein levels in lung epithelia (data not shown). Likewise, a virulent strain of the gram-negative pathogen, *P. aeruginosa* (PA103) resulted in reduced mitochondrial membrane potential and the appearance of swollen mitochondria with disrupted cristae by transmission electron microscopy. Mice infected with empty lentivirus or lentivirus encoding Fbxo7 were subsequently challenged with PA103, and then euthanized to collect lung lavage fluid and harvest tissues. We found that Fbxo7 overexpression significantly augmented pulmonary injury in this preclinical pneumonia model. Compared to an empty lentivirus control group, intratracheal introduction of Fbxo7 alone significantly increased bronchoalveolar lavage (BAL) protein concentration, lavage cell counts, and cell infiltrates (FIG. 3A, B, G). Fbxo7 overexpression also increased the release of proinflammatory cytokines TNF⟨, IL-1 and IL-6 in the lung (FIG. 3D-F). PA103 infection combined with Fbxo7 overexpression in the lung further accentuated acute lung injury, indicated by increased lavage protein concentration, cell counts, cytokines and cell infiltrates, compared to the control group or each component administered individually. However, overexpressed Fbxo7 did not alter the lavage bacterial load (FIG. 3C). In mouse lung tissue, PA103 infection compared to control induced endogenous Fbxo7 protein levels, with a corresponding reduction in Pink1 content (FIG. 3H). Compared to the Fbxo7 overexpression group, additional PA103 infection augmented this reduction of Pink1 protein levels. These data as a whole indicate that Fbxo3 pulmonary gene transfer is sufficient to trigger tissue inflammatory injury, a process that is further accentuated with concomitant *P. aeruginosa* infection. Thus, Fbxo7 functions as a proinflammatory protein in vivo.

Figure 4A:
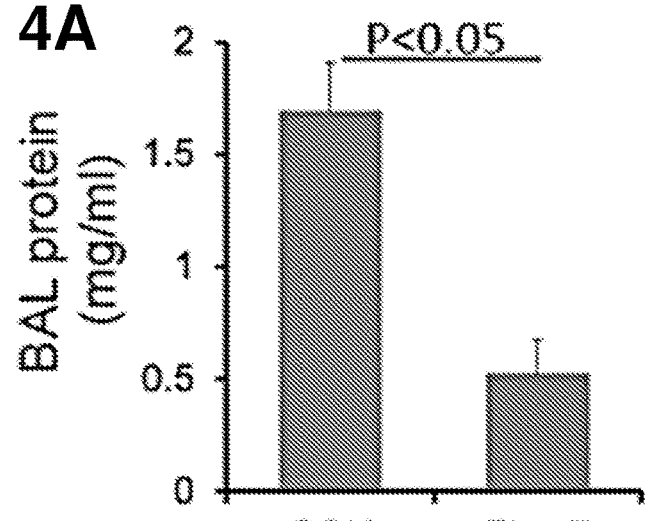
FIGS. 4A-4H. Fbxo7 knockdown attenuates bacterial-induced experimental lung injury. C57BL/6J mice were administered i.t. with Lenti-control shRNA or Lenti-Fbxo7 shRNA (108 PFU/mouse) for 144 h. Mice were then euthanized and lungs were lavaged with saline, harvested, and then homogenized. Lavage protein, cell count, bacteria loads and cytokine secretion were measured in (FIG. 4A-4F).
Figure 4B:
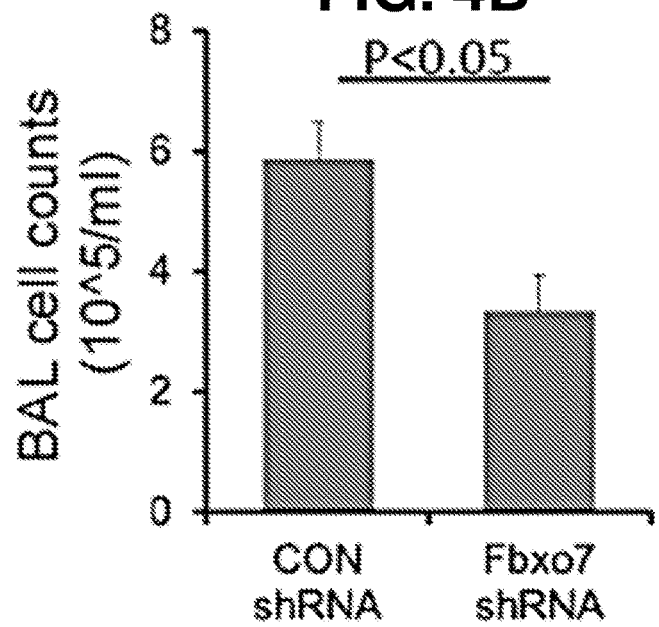
Figure 4C:
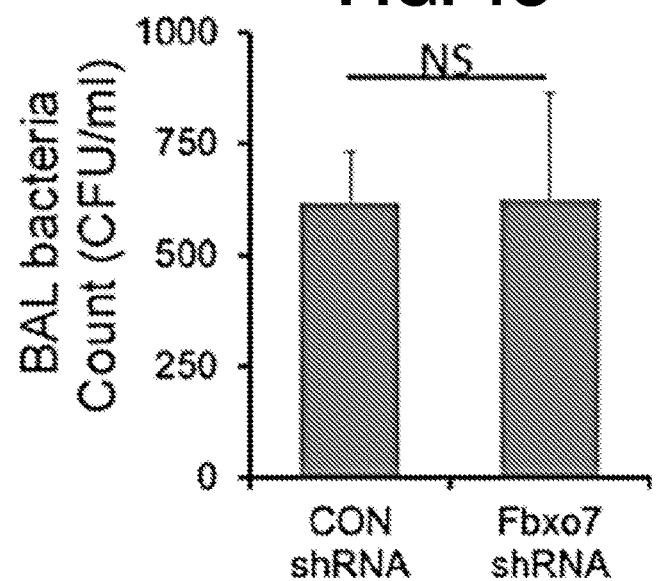
Figure 4D:
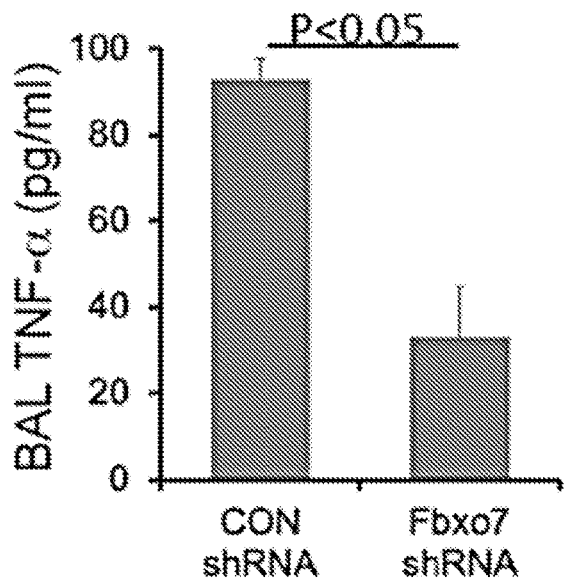
Figure 4E:
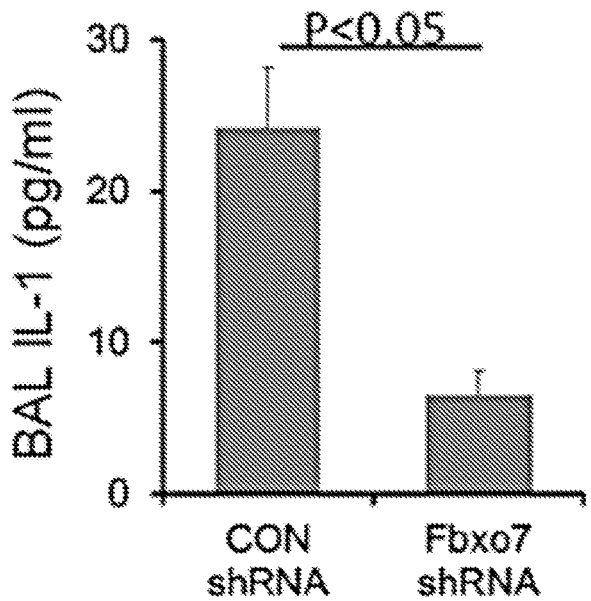
Figure 4F:
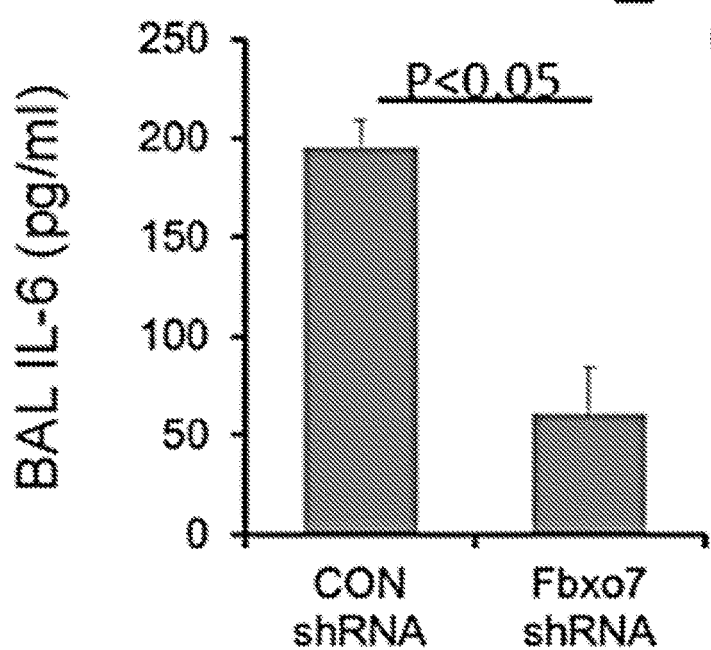
Figure 4G:
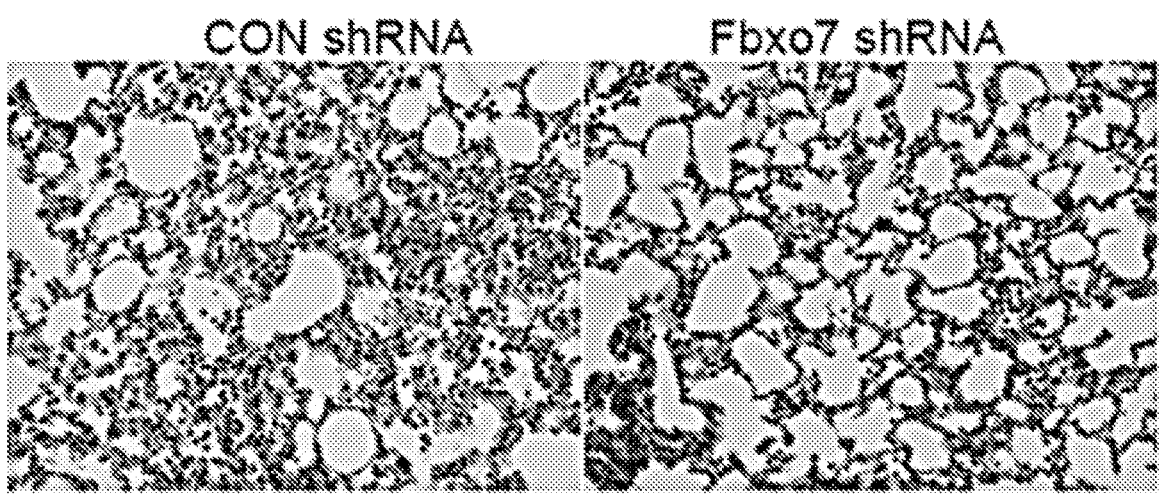
Figure 4H:
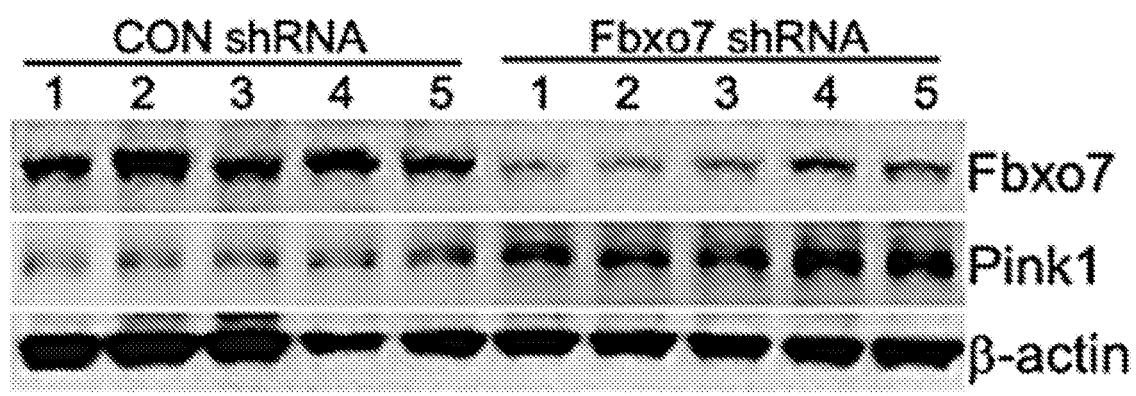

We next examined the role of Fbxo7 knockdown during *P. aeruginosa* infection. Compared to a lentiviral shRNA control group, mice infected with lentiviral Fbxo7 shRNA showed decreased protein concentration and cells in BAL without altering bacterial counts (FIG. 4A-C). Additionally, Fbxo7 knockdown decreased the release of pro-inflammatory cytokines and exhibited histological evidence of reduced tissue cell infiltrates (FIGS. 4D-G). Immunoblotting data from lungs confirmed that Fbxo7 knockdown restored Pink1 protein levels despite bacterial infection (FIG. 4H). Collectively, these in vivo studies suggest for that Fbxo7 plays an integral role in regulating the inflammatory response via the Pink1-cytokine axis and may serve as a potential pharmacologic target.

Figure 5A:
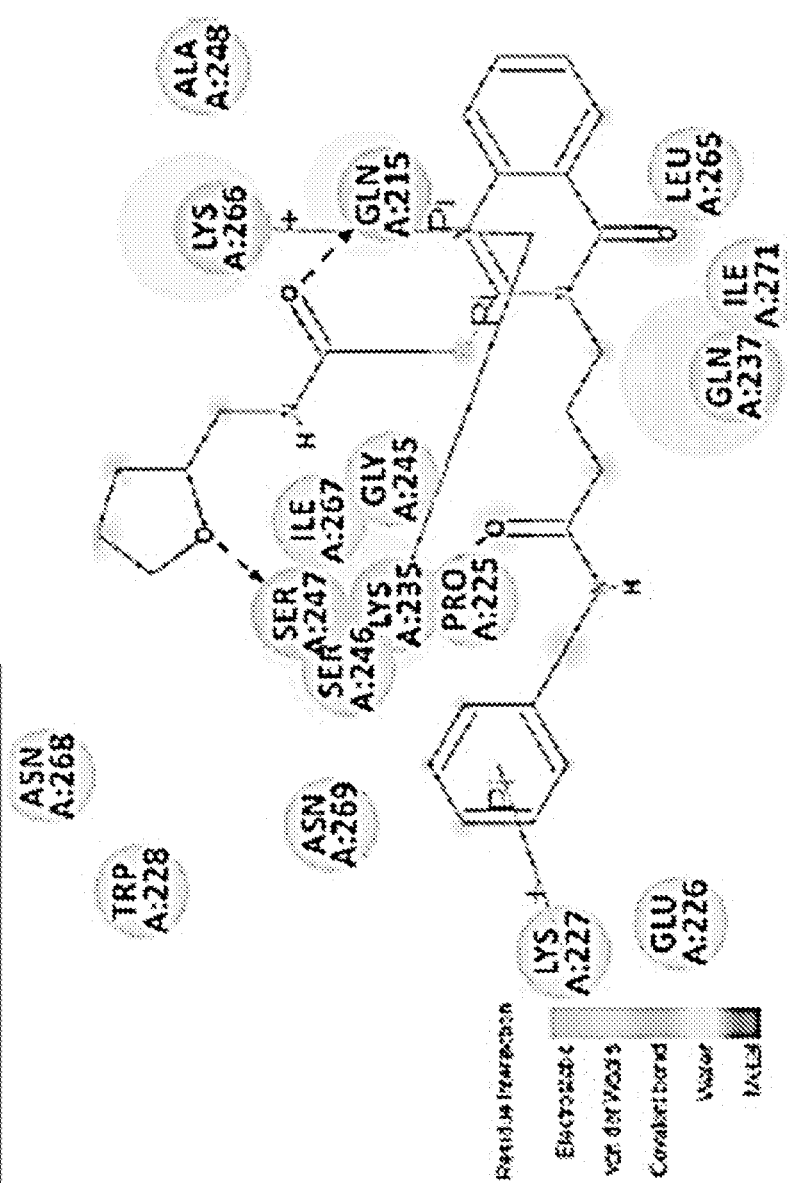
Figure 5A:
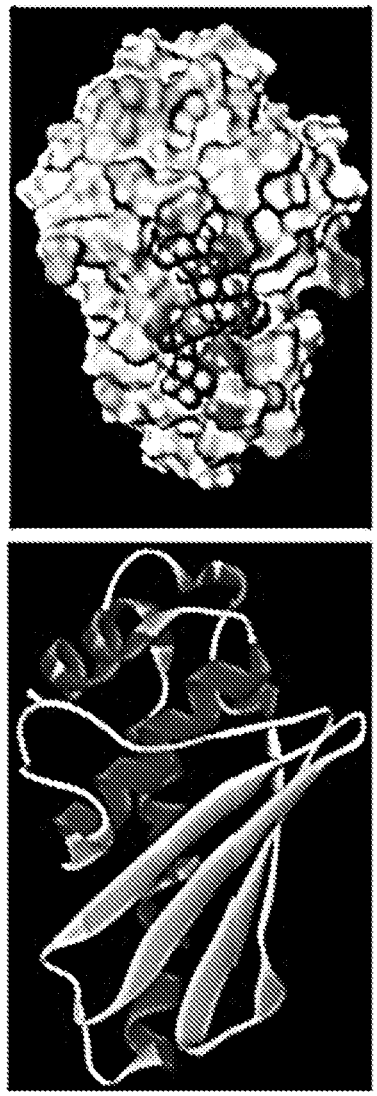
Figure 5D:
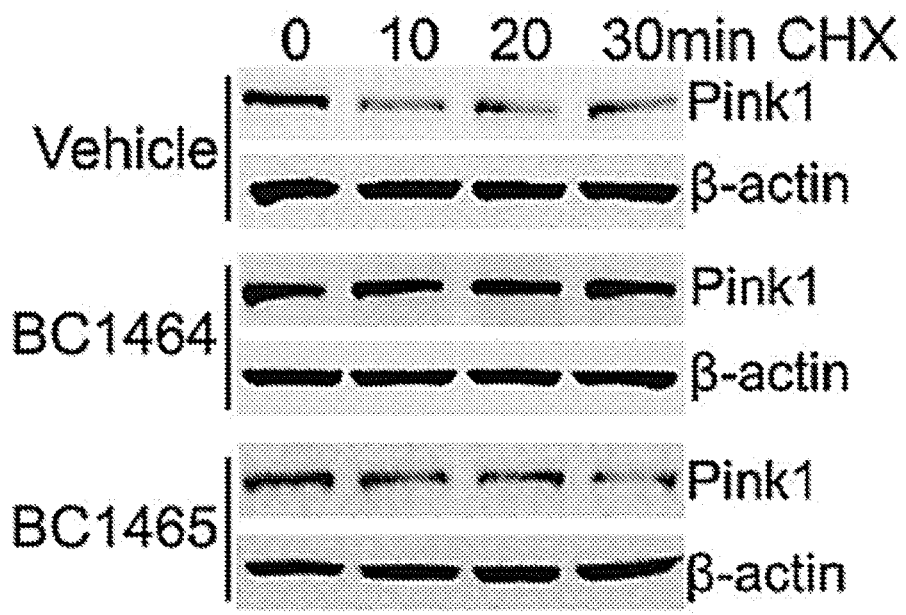
Figure 5G:
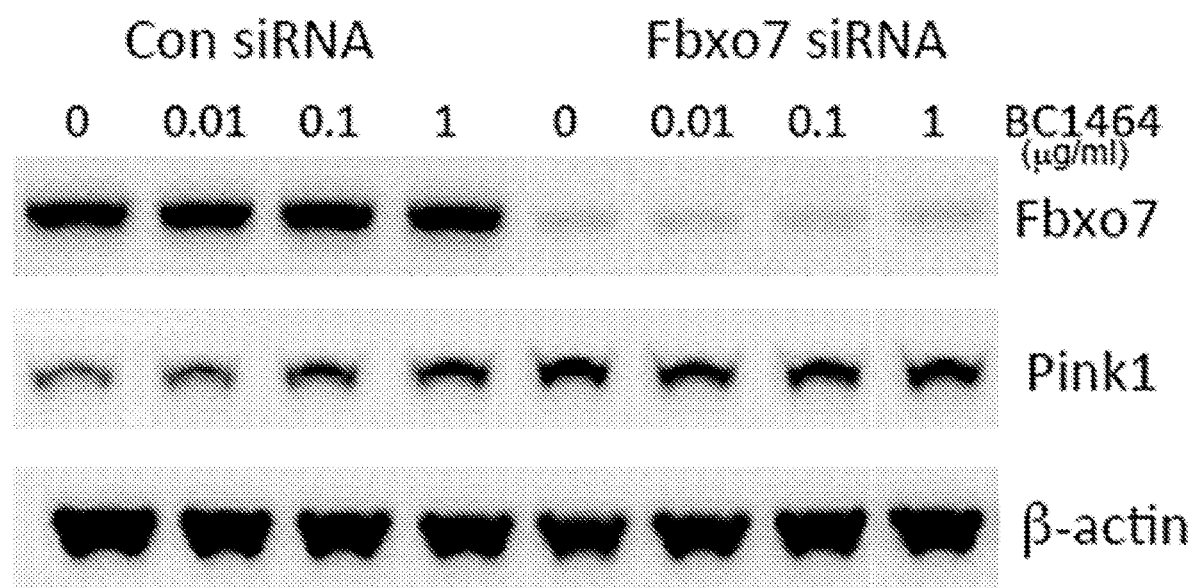
Figure 5E:
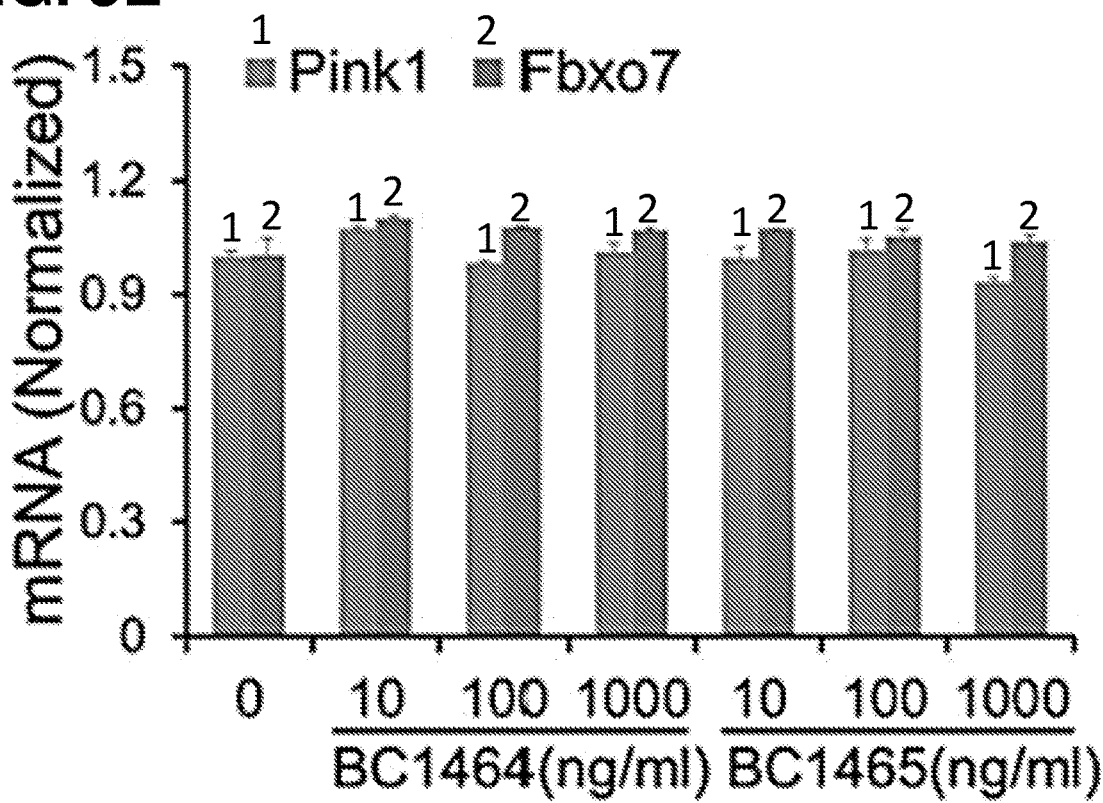
Figure 5F:
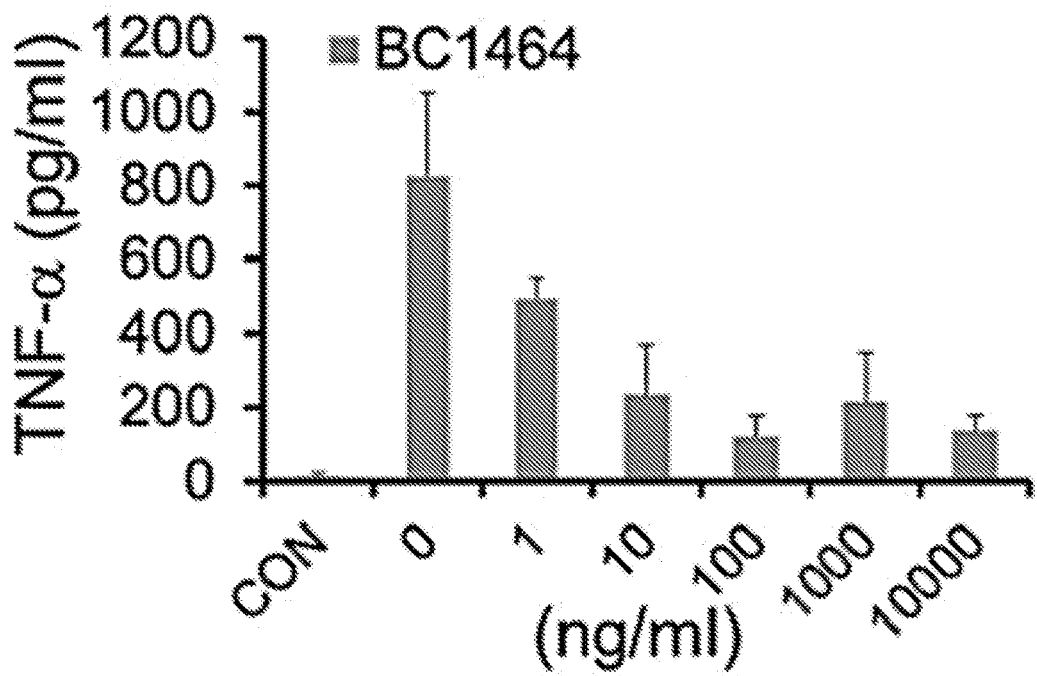

To further investigate Fbxo7 targeting in experimental pneumonia, we analyzed Fbxo7 structure and designed small molecule inhibitors. Fbxo7 harbors a conserved FP domain within its C-terminus, which is crucial for its interaction with substrates or regulatory proteins. Since the FP domain confers E3 ligase activity through substrate binding, we hypothesized that small molecule inhibition of the FP domain will induce a conformational change, thereby disrupting ability of Fbxo7 to capture Pink1. We constructed a homology model using the FP domain crystal structure (4L9C.pdb) (FIG. 5A). Using molecular docking analysis and scored-ranking operations on the Fbxo7-FP domain 3-D structure model, we assessed potential ligands that might fit the FP domain cavities. These docking experiments were conducted using the LibDock program from Discovery Studio 3.5. A library containing 500 k small molecule compounds was first used to screen potential ligands for the Fbxo7-FP domain. The top ten score-ranking molecules were selected and further evaluated using in vitro experiments. In this model, GLN215, LYS227, LYS235, SER247 and LYS266 residues within the FP domain are important for interacting with inhibitors (FIG. 5A). Thus, we tested if BC1464 affected the interaction between Fbxo7 and Pink1. The in vitro binding assay demonstrated that increasing amounts of BC1464 efficiently decreased the interaction between Fbxo7 and Pink1 (FIG. 5B). BC1464 also increased Pink1 protein levels in cells in a dose dependent manner (FIG. 5C). Endogenous full length Pink1 rapidly degrades upon inhibiting protein synthesis. However, addition of BC1464 largely stabilized Pink1, while compound BC1465 showed no effect on Pink1 protein stability (FIG. 5D). Neither BC1464 nor the control compound, BC1465, affected the mRNA levels of Pink1 or of Fbxo7 (FIG. 5E). Further, in human PBMCs, the LPS stimulated release of the pro-inflammatory cytokine TNF (was reduced ~37% at 1 ng/ml and potently blocked at 10 ng/ml of BC1464 (FIG. 5F). Last, to assess target validation, we depleted Fbxo7 and added BC1464 to cells. As expected, Fbxo7 siRNA caused a basal increase in Pink1 levels. While the addition of compound elicited a dose-dependent increase in Pink1 levels in control cells with normal levels of Fbxo7, this was not observed after Fbxo7 siRNA treatment (FIG. 5G). These results indicate that small molecule inhibition of the association of Fbxo7 with Pink1 protects the kinase from SCFFbxo7 mediated degradation resulting in reduced agonist-induced inflammation in human pro-inflammatory cells.

Figure 6A:
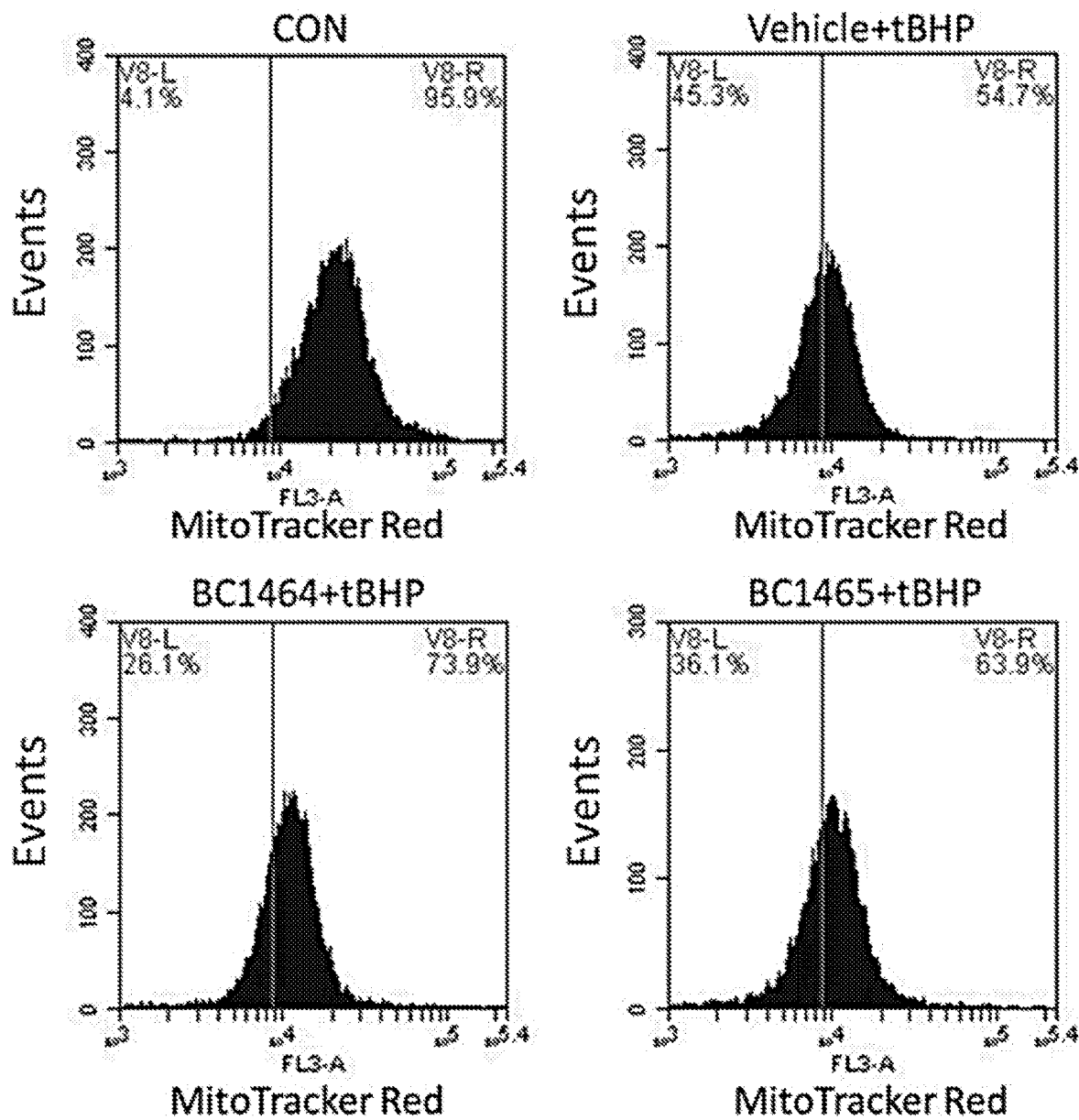
FIGS. 6A-6D. Fbxo7 small molecule inhibitor protects mitochondria.
Figure 6B:
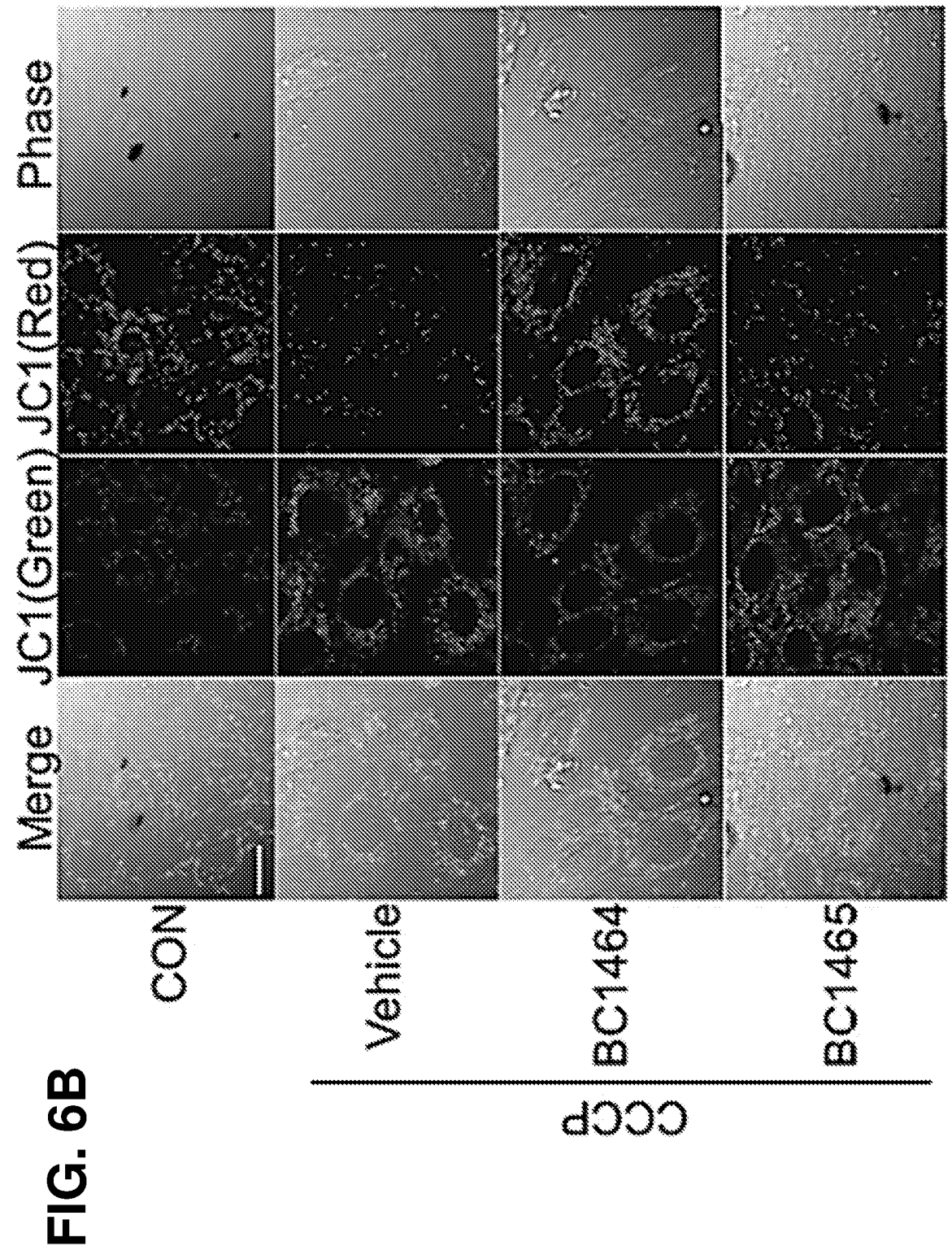
Figure 6C:
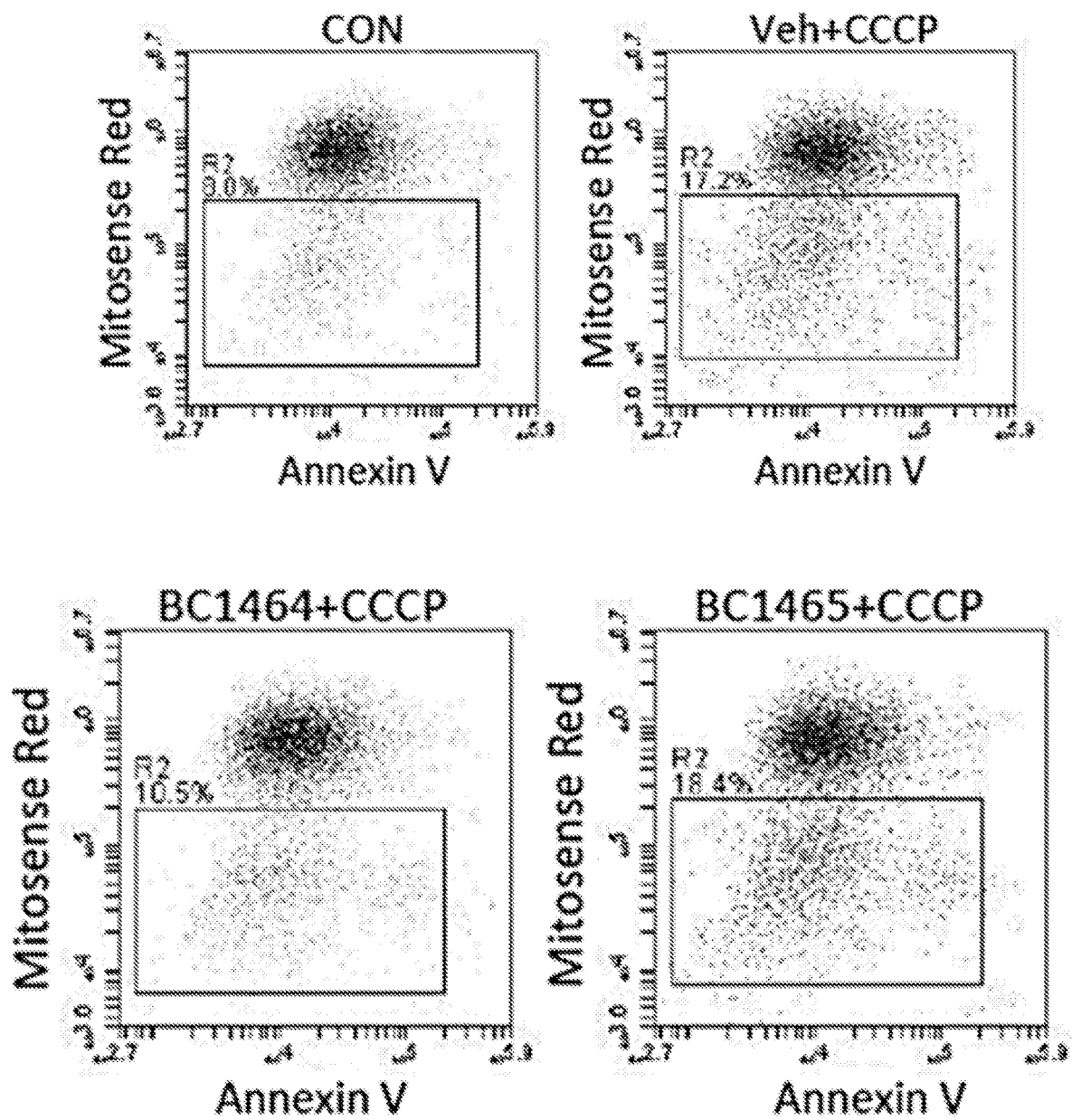
Figure 6D:
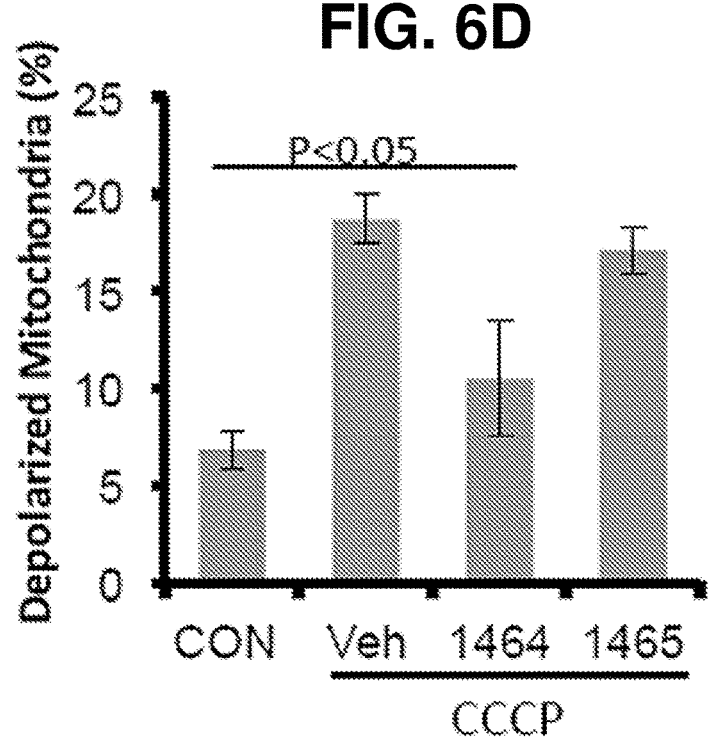

Next, we examined if small molecule inhibition of Fbxo7 modulates mitochondrial function. In rat myoblast H9C2 cells, rich in mitochondria, a reactive oxygen species (ROS) inducer tert-Butyl hydroperoxide (tBHP) potently increased numbers of damaged mitochondria from 4.1% to 45.3%, as shown using MitoTracker Red staining combined with flow cytometry analysis (FIG. 6A). Pretreatment with BC1464 largely protected mitochondria from oxidative stress triggered by tBHP compared to its vehicle control, as indicated by a significant reduction in mitochondrial injury from 45.3% to 26.1%. In contrast, BC1465 displayed less effective ability to prevent tBHP-induced mitochondrial injury. JC1 staining further demonstrated that BC1464 maintains the mitochondrial membrane potential disrupted by CCCP, compared to the control vehicle and BC1465 groups (FIG. 6B). BC1464 also prevented CCCP triggered mitochondrial injury as assessed using Mitosense Red and Annexin V staining, decreasing the numbers of CCCP damaged mitochondria from 17.2% to 10.5% (FIG. 6C,D). These data suggest that a Fbxo7 inhibitor that preserves Pink1 levels supports the maintenance of mitochondrial structure and function after pro-oxidant stress.

Figure 7A:
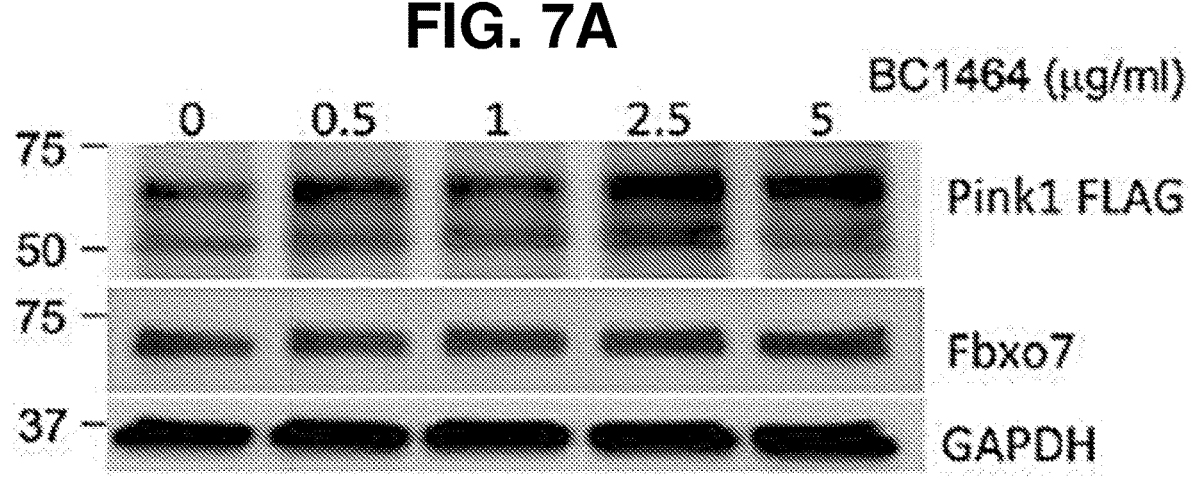
Figure 7D:
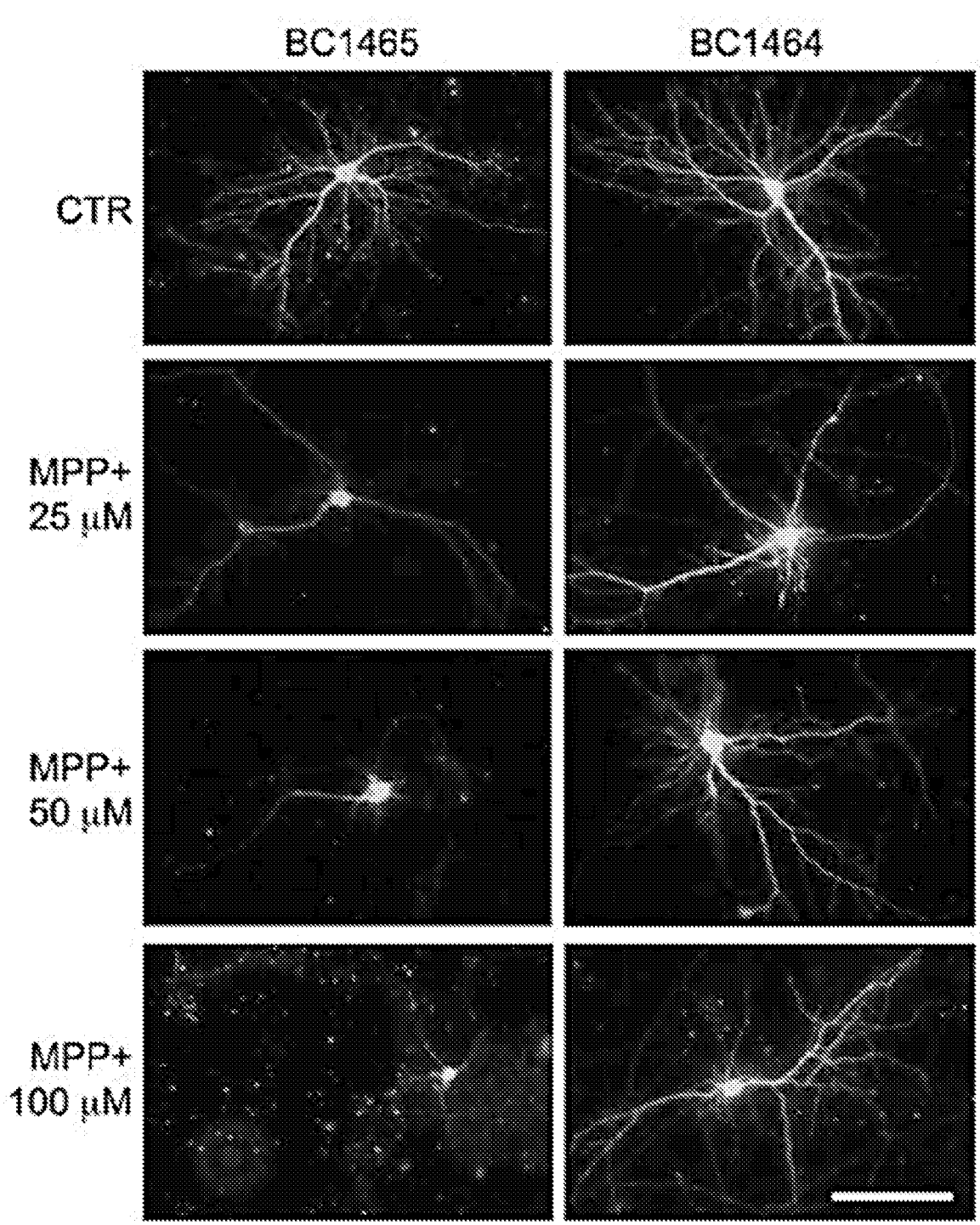
Figure 7E:
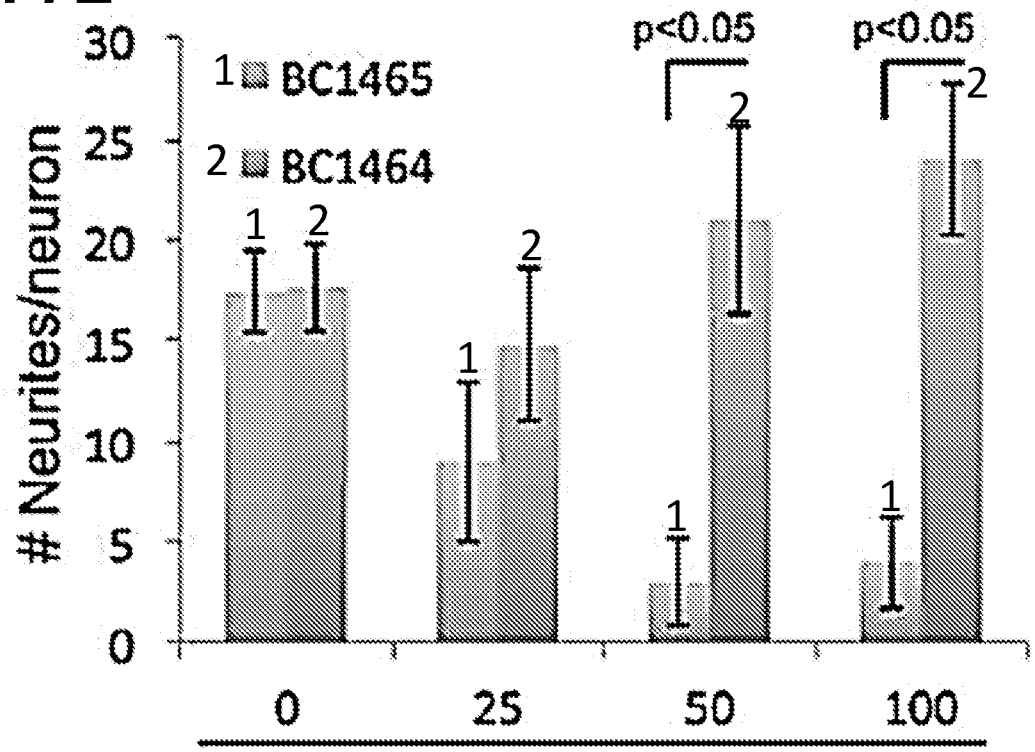

We next expanded preclinical studies to humanized and primary cell models. As Pink1 mutations are linked to neurodegenerative disorders such as Parkinson's disease, we tested BC1464 in two neuronal cell systems. First, we established that human SH-SY5Y neuroblastoma cells express Fbxo7, and that BC1464 stabilizes PINK1 expression in the presence of cycloheximide in neuronal cells (FIG. 7A). Next we studied the effects of BC1464 on neuronal cell injury induced by the complex I inhibitor 1-methyl-4-phenylpyridinium (MPP+). Parkinson's disease is characterized by reduced complex I activity and MPP+, the active metabolite of 1-methyl-4-phenyl-1,2,3,6-tetrahydropyridine (MPTP), which causes a human parkinsonian syndrome, is frequently used to model parkinsonian cell death. We found that BC1464 significantly decreased MPP+ elicited injury in human SH-SY5Y cells relative to the inactive control BC1465 (FIG. 7B). Likewise, in primary cortical neurons (FIG. 7C) the Fbxo7 inhibitor BC1464 protected against the cytotoxic effects of MPP+. Neurodegeneration is characterized by neurite retraction, a phenotype that is not generally reversed even if cell death is arrested. Thus, we examined the effects of BC1464 versus BC1465 on a morphological index of dendritic injury in primary cortical neurons. We found that BC1464 was able to not only reduce cell death, but also protect against retraction and simplification of the dendritic arbor (FIGS. 7D and 7E).

Figure 7F:
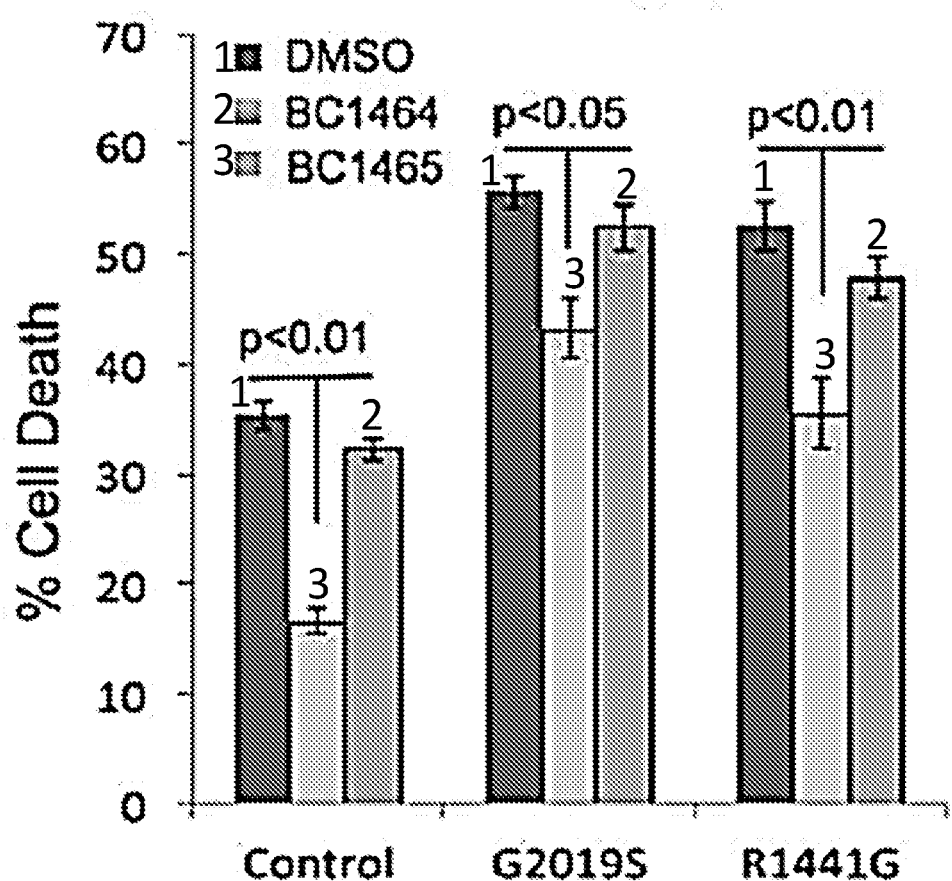

We obtained fibroblasts from control and two Parkinson's disease patients with different mutations in leucine-rich repeat kinase (LRRK2) linked to an autosomal dominant form of Parkinson's disease. There were no basal effects of the mutations on fibroblast viability. When we applied the Parkinsonian toxin MPP+, we noted increased sensitivity of the two patient-derived fibroblasts, but the BC1464 compound conferred significant protection in all three primary human fibroblast cultures (FIG. 7F). We also found that BC1464 conferred protection in the 6-hydroxydopamine (6-OHDA) model of Parkinson's disease (FIG. S3).

Figure 7G:
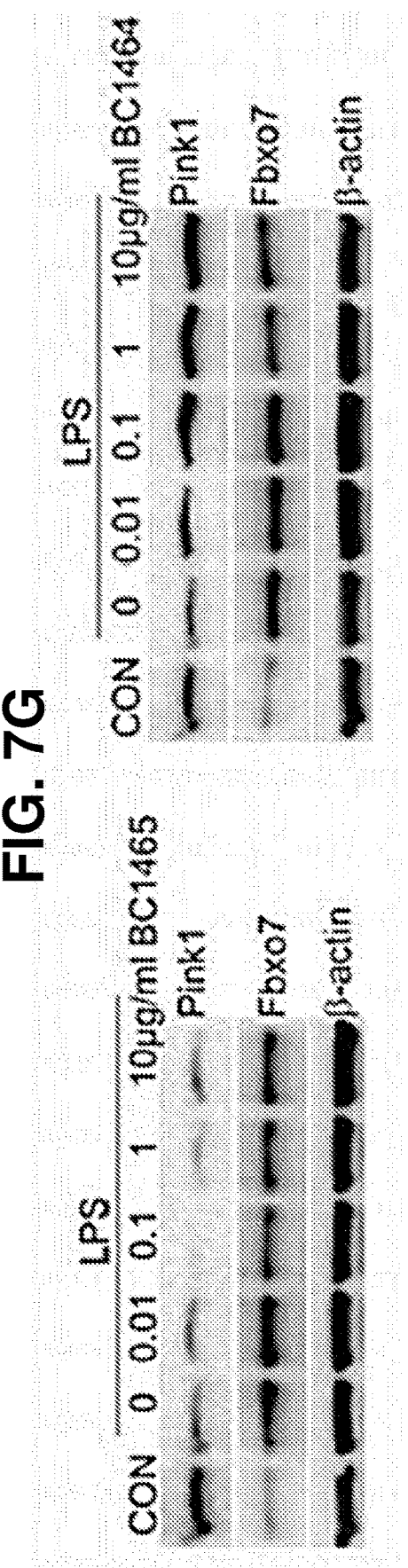
Figure 7H:
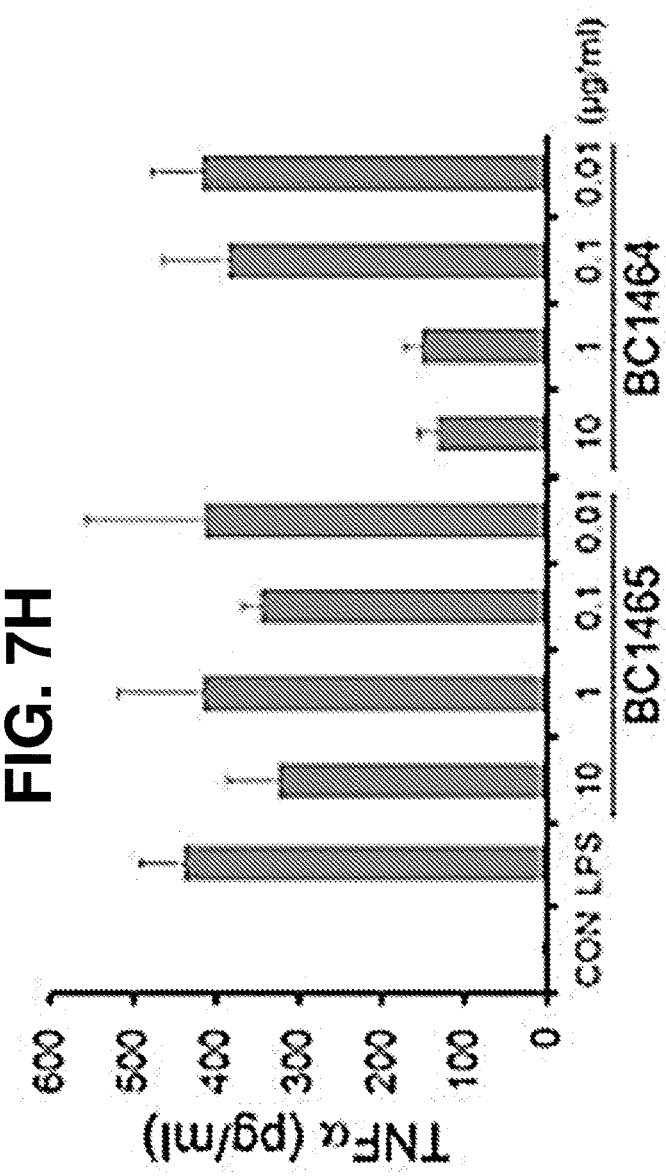
Figure 8A:
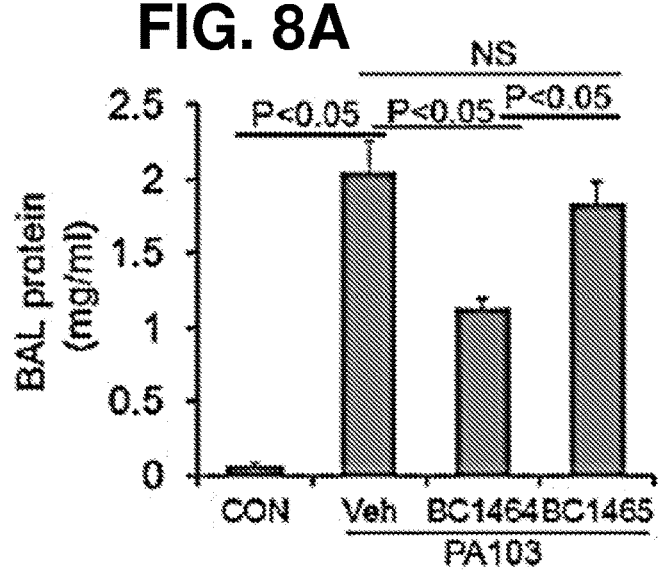
FIGS. 8A-8H. Fbxo7 small molecule inhibitor attenuates severity of experimental pneumonia. C57BL/6J mice (5-6 mice/group) were administered i.t. with PA103 (104 PFU/mouse). BC-1464 was given through an intraperitoneal injection (5 mg/kg) at the same time. Compound BC1465 served as a negative control. 18 h later, mice were euthanized, and lungs were lavaged with saline, harvested, and then homogenized. Lavage protein, cell count, bacteria loads and cytokine secretion were measured in FIG. 8A-8F.
Figure 8B:
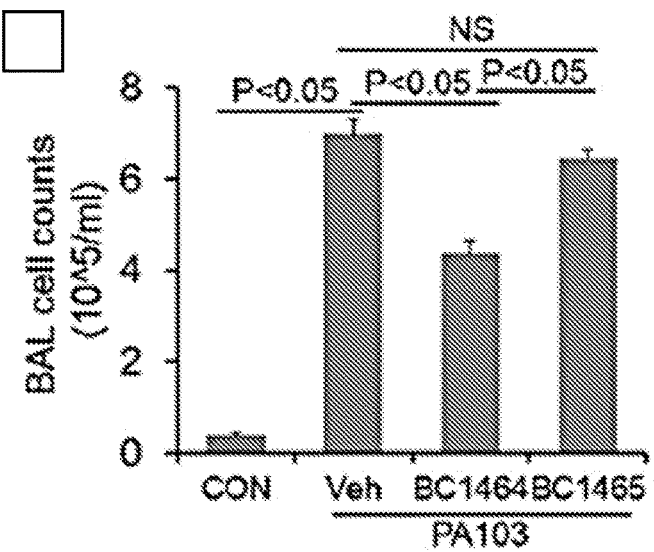
Figure 8C:
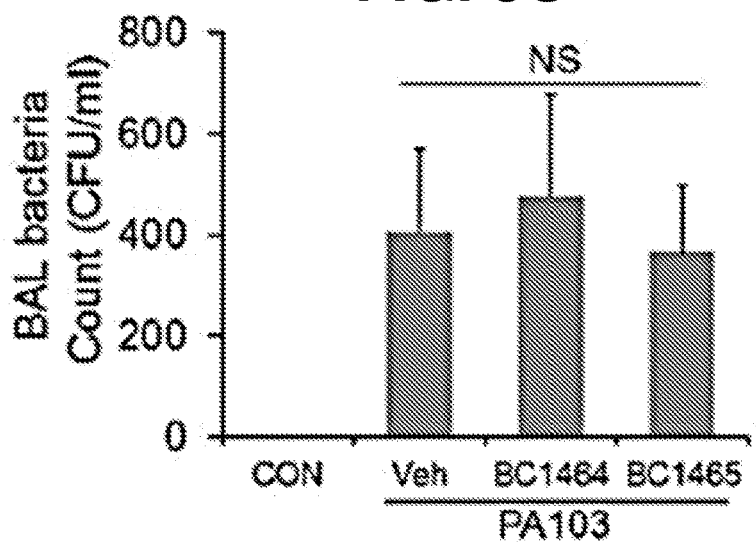
Figure 8D:
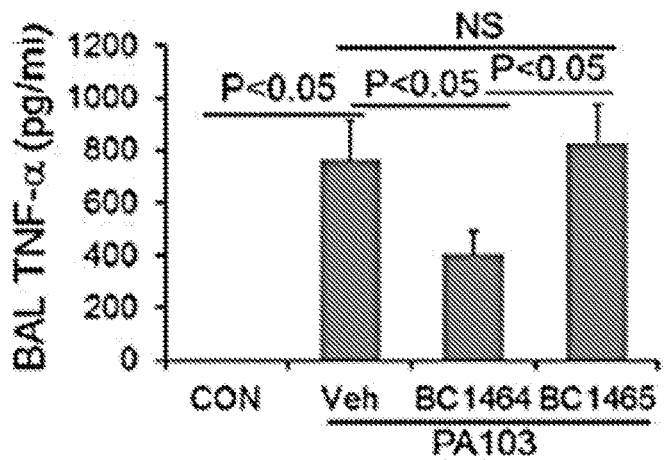
Figure 8E:
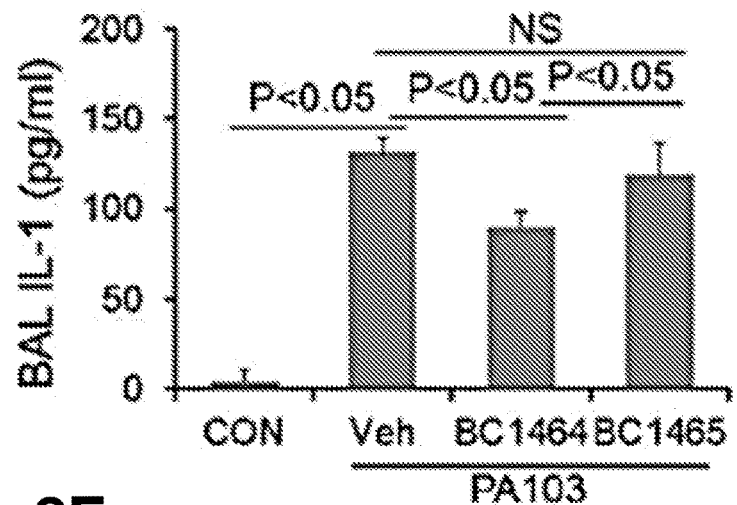
Figure 8F:
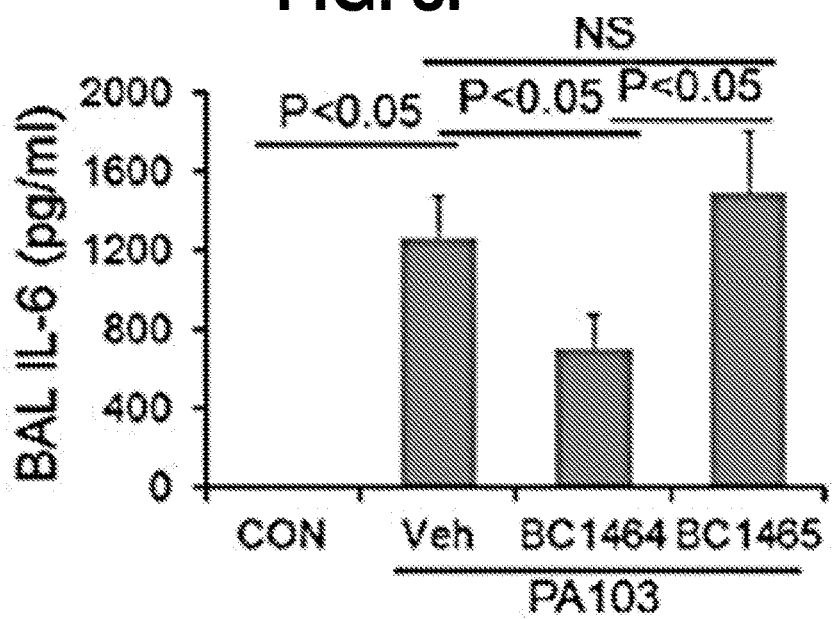
Figure 8G:
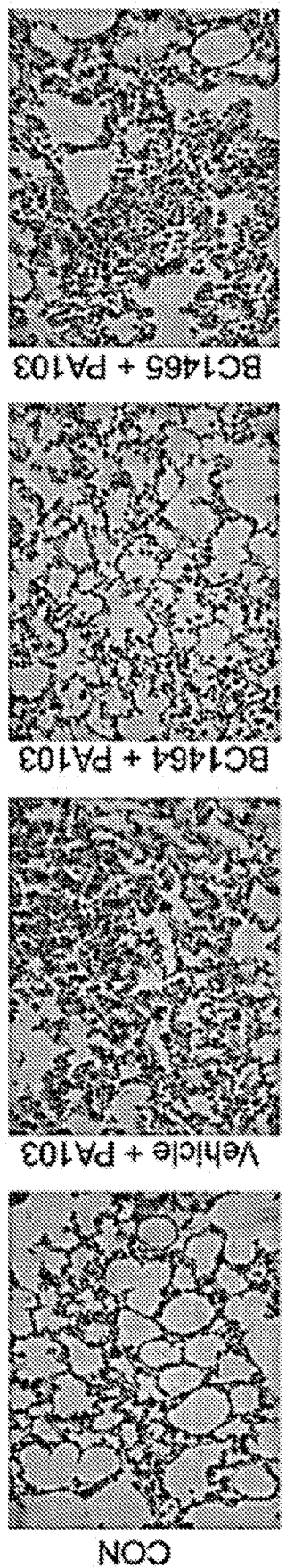
Figure 8H:
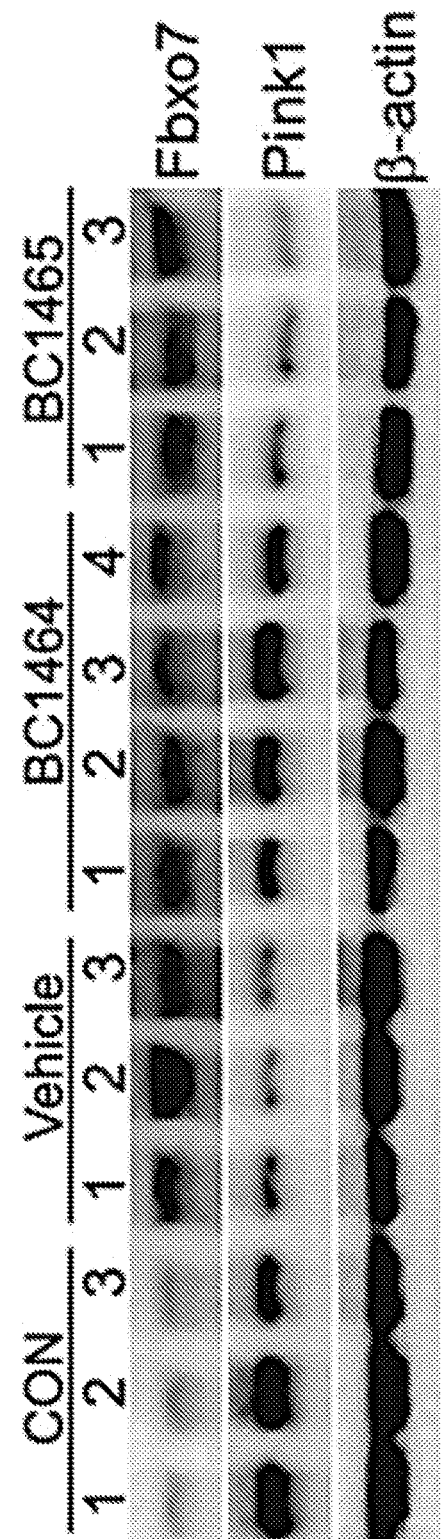

Next we examined the effects of the Fbxo7 inhibitor in a phenotypic screen using human lung explants. Here, BC1464 was observed to selectively increase Pink1 protein levels and inhibit cytokine release in response to endotoxin (FIG. 7G,H). Finally, we tested the Fbxo7-Pink1 docking inhibitor compounds in experimental pneumonia. Consistent with our previous observations, PA103 infection potently triggered lung inflammatory injury (FIGS. 8A, B, and G). BC1464 had no effect on lavage bacteria counts (FIG. 8C). However, compared to either the vehicle control or the BC1465 group, administration of BC1464 significantly decreased lavage protein, cell numbers, and cytokine levels (FIG. 8D-F). Taken together, it is clear that BC1464 stabilizes Pink1 expression and exerts cytoprotective activity in a variety of human and mouse cell types and injury models. Compound BC1464 Protects Against DMSO-Induced Cell Death in Late Neural Progenitor Cells Differentiated from a Human iPSC Line Derived from a Parkinson's Disease Patient with Triplication of the SNCA Gene.

Methods. Late neural progenitor cells were derived from an iPSC line from a PD patient with SNCA gene triplication, as previously described (D'Aiuto et al. *Organogenesis* 10(4): 365-377). Rosettes were seeded on Matrigel coated Ibidi plates and cells grown for 3 wks in Neurobasal (NB) media (Gibco #21103049) supplemented with B27 and BDNF (Invitrogen #RP8642) before treatment with DMSO or 5 ng/mL of BC1464 or BC1465 for 1 wk and stained with DAPI to identify nuclei. Images were acquired with a 40× oil objective (1.30 NA) on an Olympus IX71 microscope using Olympus CellSens V1.17 with a DP80 camera. Cell death was assessed by counting condensed/fragmented nuclei.

Figure 9:
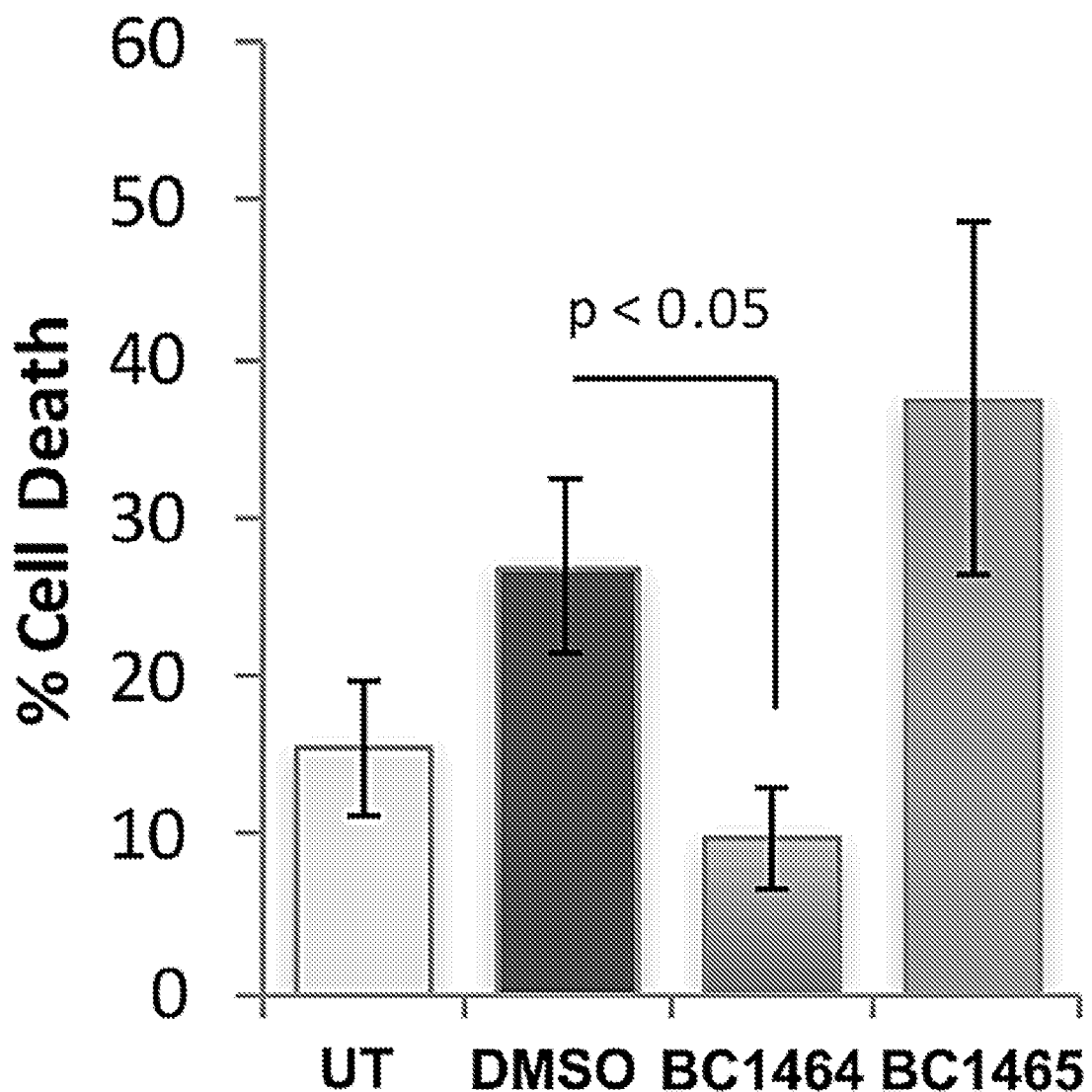
FIG. 9 is a graph showing compound BC1464 protects against DMSO-induced cell death in late neural progenitor cells differentiated from a human iPSC line derived from a Parkinson's disease patient with triplication of the SNCA gene.

Results. Triplication of the SNCA gene that encodes alpha-synuclein is a cause of autosomal dominant Parkinson's disease and Dementia with Lewy bodies (Singleton, A. B. et al. *Science* 302, 841 (2003). Preliminary data indicate that cells differentiated from an SNCA triplication iPSC line exhibit elevated cell death when exposed to DMSO. BC1464, but not BC1465, prevented toxicity elicited by DMSO in neural progenitor cells differentiated from a PD patient with the SNCA triplication (FIG. 9).

Preliminary studies indicate that mice can survive administration of 10 ug/ml of the compound via intracerebral ventricular infusion for 2 weeks, so there is no overt toxicity. BC1464 was administered in artificial CSF with DMSO by intracerebroventricular pump to C5bl/6 mice.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating a neurodegenerative disease or an inflammatory disorder in a subject, comprising administering to the subject in need thereof, a compound, or a pharmaceutically acceptable salt thereof, of formula II:

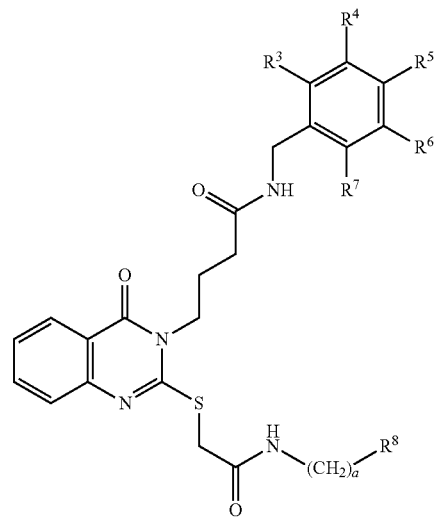

wherein each of $R^3$-$R^7$ is independently H, halogen, optionally-substituted alkyl, amino, alkoxy or hydroxy;

$R^8$ is an optionally-substituted heterocycloalkyl; and a is 0 to 3.

2. The method of claim 1, wherein the compound is:

3. A method for treating frontotemporal dementia, a mitochondrial disease caused by mutations in nuclear DNA, a mitochondrial disease caused by mutations in mtDNA, or a disease of skeletal or cardiac muscle in a subject, comprising administering to the subject in need thereof, a compound, or a pharmaceutically acceptable salt thereof, of formula II:

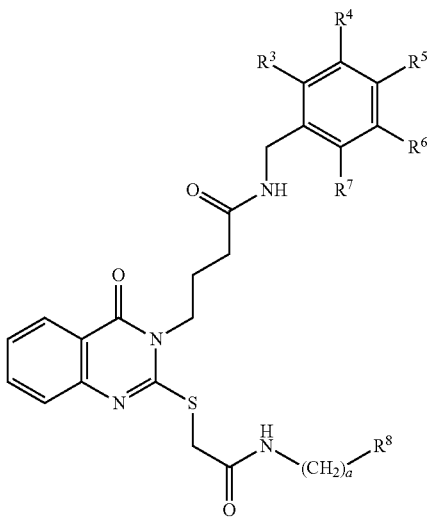

wherein each of $R^3$-$R^7$ is independently H, halogen, optionally-substituted alkyl, amino, alkoxy or hydroxy; $R^8$ is an optionally-substituted heterocycloalkyl; and a is 0 to 3.

4. The method of claim 1, wherein the subject is in need of treatment for Parkinson's disease and the compound is:

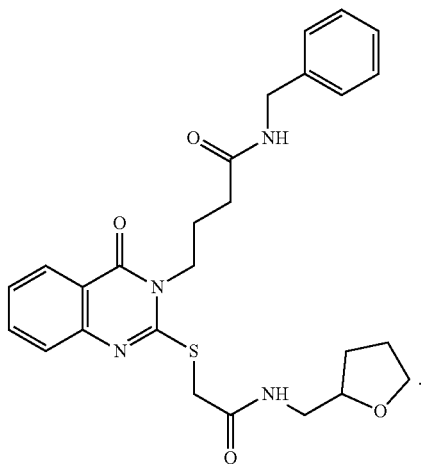 [SMILES: O=C(CCCn1c(SCC(=O)NCC2CCCO2)nc2ccccc2c1=O)NCc1ccccc1]

5. The method of claim 1, wherein the subject is need of treatment for a neurodegenerative disease.

6. The method of claim 1, wherein at least one of $R^3$-$R^7$ is an aminoalkyl.

7. The method of claim 1, wherein the aminoalkyl is —$(CH_2)_b$—$NR^9R^{10}$, wherein $R^9$ and $R^{10}$ are each independently H or alkyl and b is 1 to 5.

8. The compound of claim 1, wherein at least one of $R^3$-$R^7$ is an amino.

9. The method of claim 8, wherein the amino is —$NH_2$ or an alkylamino.

10. The method of claim 9, wherein the alkylamino is —$NR^{11}R^{12}$, wherein $R^{11}$ and $R^{12}$ are each independently H or alkyl.

11. The method of claim 1, wherein at least one of $R^3$-$R^7$ is an alkoxy.

12. The method of claim 1, wherein $R^5$ is not H.

13. The method of claim 1, wherein $R^5$ is alkoxy or alkylamino.

14. The method of claim 1, wherein at least two of $R^3$-$R^7$ are halogen.

15. The method of claim 1, wherein at least one of $R^3$-$R^7$ is not H.

16. The method of claim 1, wherein each of $R^3$-$R^7$ is H.

17. The method of claim 1, wherein $R^8$ is a 5-membered heterocycloalkyl or a 6-membered heterocycloalkyl.

18. The method of claim 1, wherein $R^8$ is a heterocycloalkyl that includes at least one oxygen heteroatom.

19. The compound of claim 1, wherein the heterocycloalkyl is selected from oxetanyl, dioxetanyl, oxolanyl, dioxolanyl, oxanyl or dioxanyl.

20. The method of claim 1, wherein the heterocycloalkyl is oxolanyl or oxanyl.

21. The method of claim 1, wherein $R^8$ is:

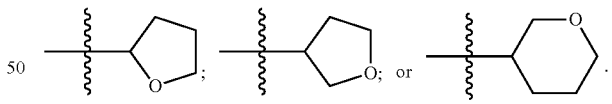

* * * * *